United States Patent [19]
Park et al.

[11] Patent Number: 5,990,126
[45] Date of Patent: Nov. 23, 1999

[54] QUINOLINIC SULFIDE DERIVATIVES ACTING AS NMDA RECEPTOR ANTAGONISTS AND PROCESS FOR PREPARATION THEREOF

[75] Inventors: No Sang Park; Churl Min Seong; Young Sik Jung; Jin Il Choi; Chang Woo Lee; Yong Jun Chung, all of Taejon-si; Seung Won Choi, Seoul; Jae Yang Kong, Taejon-si; Woo Kyu Park, Chungjoo-si, all of Rep. of Korea

[73] Assignee: Korea Research Institute of Chemical Technology, Taejon-si, Rep. of Korea

[21] Appl. No.: 09/052,752

[22] Filed: Mar. 31, 1998

[30] Foreign Application Priority Data

Mar. 31, 1997 [KR] Rep. of Korea .................. 97-11958
Apr. 15, 1997 [KR] Rep. of Korea .................. 97-13818
Nov. 6, 1997 [KR] Rep. of Korea .................. 97-58546

[51] Int. Cl.$^6$ .......................... A61K 31/47; C07D 215/22
[52] U.S. Cl. ............................................ 514/312; 546/155
[58] Field of Search ............................. 514/312; 546/155

[56] References Cited

FOREIGN PATENT DOCUMENTS 0481676 4/1992 European Pat. Off. .
94/20470 9/1994 WIPO .

OTHER PUBLICATIONS

Pongratz, E. et al.: Ylide von heterocyllen,VIII'. Monatshefte fur chemie vol. 115, pp. 231–242, 1984.

*Primary Examiner*—John Kight
*Assistant Examiner*—Charanjit S. Aulakh
*Attorney, Agent, or Firm*—Dilworth & Barrese

[57] ABSTRACT

A class of quinolinic sulfide derivatives of formula I are potent and specific antagonists at the strychnine insensitive glycine bitding site on the NMDA receptor complex with an pharmacological advantageous profile. They may be useful in treatment or prevention of neuro-degenerative disorders. Particularly, the compounds included in the present invention are especially useful for minimizing damage of the central nervous system arising as a consequence of ischemic or hypoxic condition such as stroke, hypoglycemia, cerebral ischemia, cardiac arrest, and physical trauma. They are also useful in prevention of chronic neurodegenerative disorders including epilepsy, Alzheimer's disease, Huntington's disease and Parkinsonism. By virtue of their NMDA receptor antagonist properties, the present compounds may also use as anticonvulsant, analgesic, antidepressant, anxiolytic, and antischizophrenic agent. Formula I

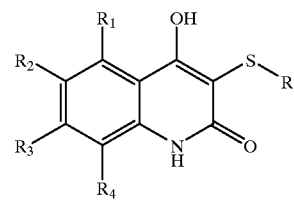

wherein $R_1$, $R_2$, $R_3$, $R_4$, and R are defined in specification.

16 Claims, No Drawings

QUINOLINIC SULFIDE DERIVATIVES ACTING AS NMDA RECEPTOR ANTAGONISTS AND PROCESS FOR PREPARATION THEREOF

FIELD OF THE INVENTION

The present invention relates to therapeutically active quinolinic sulfide derivatives acting as potent and specific antagonists of excitatory amino acids, to a process for preparation and to their use in treatment in neurological disorders.

Particularly, the compounds included in the present invention show antagonism toward excitaory action of NMDA receptor, and are especially useful for minimizing damage of the central nervous system arising as a consequence of ischemic or hypoxic condition such as stroke, hypoglycemia, cerebral ischemia, cardiac arrest, and physical trauma.

They are also useful in prevention of chronic neurodegenerative disorders including epilepsy, Alzheimer's disease, Huntington's disease and Parkinsonism.

By virtue of their NMDA receptor antagonist properties, the present compounds also posses anticonvulsant, analgesic, antidepressant, anxiolytic, and antischizophrenic activities.

BACKGROUND OF THE INVENTION

Recently, the elderly represent the most rapidly growing segment of society. This growth in the aged population has placed a substantial burden on health care and social support systems because of the increase in the incidence of chronic, degenerative illness such as senile dementia. Approximately 4 millions individuals over the age of 65 in the United States (or 15% of the population) has some degree of dementia, Two thirds of them(over 2.5 millions) are affected severely, remain home sitting and relying on family and community resources for their care. Approximately 55% of all case of dementia are known as Alzheimer's disease. The Alzheimer's disease patient gradually loses verbal communication skills, as evidenced by decreased ability to relate words to objects and impaired comprehension of their verbal output. Recent research efforts provide some information about the underlying pathophysiology of this illness of dementia. And of several causal theories, the major plausible hypothesis are based on the fact that differentiation, growth, and degeneration of neuron are closely related to hyper- and hypoactivity of neurotransmitters and nerve growth factor.

The amino acid L-glutamate is the most important fast excitatory neurotransmitter in neuronal circuits in the mammalian central nervous system(CNS). Almost all CNS neurons can be excited by L-glutamate, acting on a variety of different ligand-gated ion channel cell surface receptors.

These are classified into two main categories, those for which the synthetic glutamate analogue N-methyl-D-aspartate is a potent excitant (NMDA receptors) and those on which NMDA is not active (non-NMDA). It is known that NMDA receptors, widely distributed in brain and spinal cord, are cell surface protein complex that is involved in excitatory synaptic transmission and the regulation of neuronal growth.

An unusual feature of the NMDA is that it is in-operative when target cells are in a resting state, as under such conditions of negative intracellular membrane potential the ion channel associated with the NMDA receptor is fully blocked by $Mg_{2+}$ ions. This block is voltage dependant, however, is removed if the target cell is partially depolarized by activation of non-NMDA receptors or other excitatory inputs. Thus, the NMDA receptor mechanism has a "conditional" feature, making it potentially an important "logic gate" in CNS circuits, especially relevant in processes of learning and memory.

The NMDA receptor has another unusual feature, as excessive activation of the receptor can lead to overexcitation of the target neurons to the point of cell death, probably caused by an excess accumulation of intracellular $Ca^{2+}$. Much research has focused on the role of NMDA receptors in such "excitotoxic" cell death in recent years.

Direct treatment of glutamate in vitro to cultured neuronal cells results in rapid cellular swelling followed by delayed toxicity over the subsequent 24 hours. This excitotoxicity has been shown to be $Ca^{2+}$ dependent. Following neuronal trauma a large $Ca^{2+}$ influx into the neuron through gated ion channel, such as glutamate receptors, initiates a cascade of biochemical events that disrupt normal cellular processes and can feedback to accelerate the release of glutamate and excitotoxicity. Among these events are activation of proteases and lipases, breakdown of neuronal membranes and formation of free radical, and ultimately, cell death [J. W. Mcdold, M. V. Johnson, Brain Res, Reviews 15, 41 (1990)]. A great deal of evidence has been accumulated that it plays a key role in neurodegeneration and stroke related brain cell death.

Thus, NMDA antagonists are proposed to have a number of clinical indications including ischemia and epilepsy. They may also be useful in the prevention of chronic neurodegenerative disorders such as Alzheimer's disease, Huntington's disease and Parkinsonism [G.Johnson, Annu. Rep. Med. Chem. 24, 41 (1989); G. Johnson and C. F. Bigge, ibid. 26, 11 (1991); and Werling et al., J. Pharmacol. Exp. Ther. 255, 40(1990)]. It is also believed to be central to the concept of long term potentiation (LTP), which is the persistent strengthening of neuronal connections that underlie learning and memory.

Recent report suggested that the specific glycine site ligands, 1-aminocyclopropanecarboxylic acid methyl ester, D-cycloserine and R-(+)-3-amino-1-hydroxy-pyrrolidin-2-one(HA-966) have, respectively, been proposed to be useful for promoting memory and learning in cognitive and psychiatric disorders [Bliss, T. V. P, Collingride, G. L., Nature 345, 347(1990); GB 2231048A (1990)].

NMDA receptor antagonists have also been shown to possess analgesic, antidepressant antischizophrenic and anxiolytic effects as indicated in recent reports [Dickenson, A. H. and Aydar, E., Neuroscience Lett. 121, 263(1990); R. Trullas and P. Skolnick, Eur. J. Pharmacol. 185, 1(1990); J. H. Kehne, et al., Eur. J. Pharmacol. 193, 283 (1991) and P. H. Hutson, et al., Br. J. Pharmacol. 103, 2037(1991)].

The crucial role of NMDA receptor in synaptic plasticity has been emphasized by recent developments in the understanding of the physiological functions and structural details of the subunits on the receptor. The NMDA receptor comprises a ligand gated ion channel which is subject to complex allosteric modulation at several different sites. Currently there are at least five pharmacologically distinct sites through which compounds can alter the activity of this receptor [Kumar K. N., et al., Nature 354, 70–73(1991); Nakanishi, S., et al., Nature 354, 31–37(1991); Monyer, H., et al., Science 256, 1217–1221(1992)]. They include (a) a transmitter binding site, which binds L-glutamate; (b) an allosteric modulator site, which binds glycine; (c) a site within the channel that binds phencyclidine and related compounds; (d) $Mg^{2+}$ bing site; and (e) an inhibitory divalent cation site $Zn^{2+}$ [Lynch, D. R., et al., Mol. pharmacol. 45, 540–545 (1994); Kuryatov, A., et al., Neuron 12, 1291–1300 (1994); Nakanishi, S., Science 256, 1217–1221 (1992)].

The NMDA receptor is activated by co-agonists glutamate and glycine. The associated $Ca^{2+}$ permeable channel is blocked physiologically by $Mg^{2+}$ in voltage dependent manner, and $Zn^{2+}$, which may have its own regulatory site, also decreases synaptic activity of the NMDA receptor [Lynch, D. R., et al., Mol. pharmacol. 45, 540–545(1994); Kuryatov, A. et al., Neuron 12, 1291–1300 (1994); Nakanishi, S., Science 256, 1217–1221(1992)].

Under the above circumstances, the pharmacological interest has so far been focused primarily on the NMDA receptor, and a number of potent and selective agonists and antagonists dependent on each distinct binding sites have been found as candidates for therapeutically useful agents during the last two decades. Of them, the most promising approach for regulating the NMDA receptor activity has involved in development of allosteric modulators of glycine binding site.

The stimulatory action of glycine on the NMDA receptor was studied by Johnson and Ascher who showed that the magnitude of the electrophysiological response of cultured neurons to applied NMDA is greatly reduced or absent if glycine is rigorously excluded from the external medium. Thus, the glycine site on the NMDA receptor was discovered in 1987 by them. The glycine site on the NMDA receptor is clearly distinguishable from the previously described glycine receptor, a glycine- gated chloride ion channel which is important in inhibitory synaptic transmission in spinal cord and brainstem. The latter receptor is blocked by low concentrations of the convulsant alkaloid strychinine, whereas the glycine/NMDA site is strychinine-insensitive.

Since the discovery of glycine site, there has been a rapid development of potent pharmacological agents that interact selectively with this site. A kinetic studies was suggested that the glycine- and glutamate-recognition sites exists in the same protein, and there is a negative allosteric coupling between the glycine- and glutamate-recognition sites and the binding of an agonist at glutamate-recognition site reduces the affinity of glycine for its recognition site. Similar studies also indicate that antagonist binding at glutamate recognition site is enhanced by some, but not all, glycine site antagonists and vice versa [Beneveniste, M., et al. J. Physiol. 428, 333 (1990); Leser, R. A.; Tong, G. and Jahr, C. E., J. Neurosci. 13, 1088 (1993); Clements, J. D.; Westbrook, G. L., Neuron. 7, 605 (1991)].

Recent in vivo microdialysis studies have demonstrated that in the rat focal ischemia model, there is a large increase in glutamate release in the ischemic brain region with no significant increase in glycine release [Globus, M. Y. T, et al., J. Neurochern. 57, 470–478 (1991)].

Thus theoretically, glycine antagonists should be able to diminish excessive excitation known to exist during glutamate excitotoxicity and should be very powerful neuroprotective agents, because they can prevent the opening of NMDA channels by glutamate non-competitively and therefore do not have to overcome the large concentrations of endogenous glutamate that are released in the ischemic brain region unlike competitive NMDA antagonists, i.e. modulation of the glycine site antagonists may result rather than complete inhibition of receptor function. This modulatory action might be more physiological than receptor blockage (compare with channel blockers), and thus glycine antagonists should have less propensity for side effects. That glycine antagonists may indeed be devoid of PCP-like behavioral side effects has been suggested by recent studies in which available glycine antagonists were injected directly into the brains of rodents without resulting in PCP-like behaviors [Tricklebank, M. D., et al., Eur. J. Pharmacol. 167, 127 (1989); Koek, W., et al., J. Pharmacol. Exp. Ther. 245, 969 (1989); Willets and Balster, Neuropharmacology 27, 1249 (1988)].

Such possible advantageous pharmaceutical profile of glycine site antagonists including a larger window between the desired and untoward effects of NMDA receptor blockade than other types of NMDA antagonists as well as the structural advantages of its ligands for BBB penetration makes it an attractive target for potential therapeutically useful new CNS acting drug particularly in treatment of neurological disorders.

Recent successes in identifying orally glycine receptor antagonists were reported several classes of 4-hydroxyquinolin-2(1H)-one derivatives as selective non-competitive antagonists of NMDA receptors possessing potent in vivo activity [McOuaid, L. A., et al., J. Med. Chem. 35, 3423 (1992); Leeson, P. D., et al. J. Med. Chem. 36, 3386 (1993); Kulagowski, J. J., et al., J. Med. Chem. 37, 1402 (1994); Cai, S. X., et al., J. Med. Chem. 39, 4682 (1996), and 39, 3248 (1996); EP 489,458; EP 459,561; EP 685,466 A1; WO 94/20470; WO 93/10783; EP 685,466 A1; and EP 481,676 A1]. Those have been appeared in literatures and are generally declaimed as therapeutically useful agents to prevent or treat neurodegenerative disorders, convulsion and schizophrenia.

Glycine-site antagonists have emerged on drugs acting on CNS because they have offered wide therapeutic window between the desired neuroprotective effects and adverse events such as behavioral stimulation that have been observed with competitive glutamate antagonists or channel blockers.

The followings are glycine-site antagonists which have been already developed.

2-Carboxyindole acrylamide developed by Glaxo Wellcome;

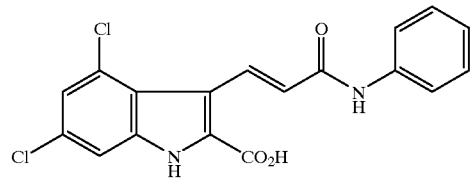

Quinoxaline-2,3-dione developed by Ciba-Geigy;

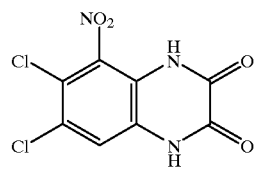

Tricyclic quinoxalinedione developed by Ciba-Geigy;

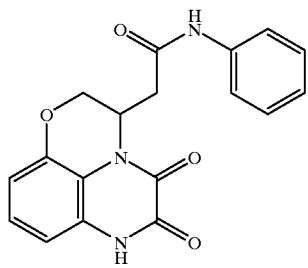

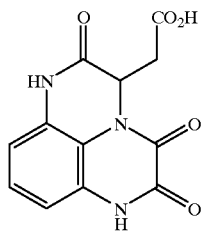

Pyridazino quinolinedione developed by Zeneca;

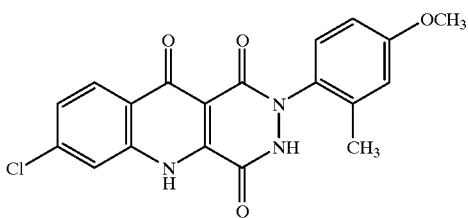

Heterocyclic compound developed by Pfizer,

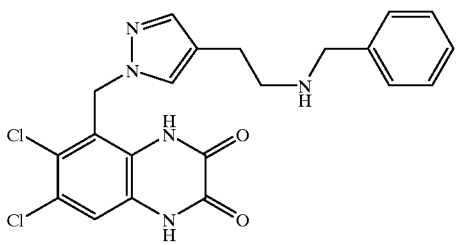

Heterocyclic compound developed by Ciba-Geigy;

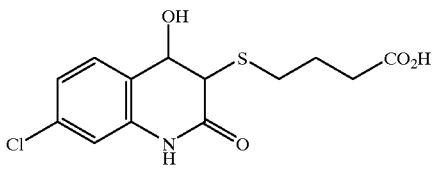

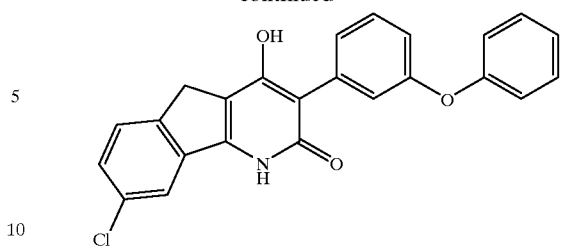

Various compounds including above examples have been developed, but the compound, which has good CNS penetration and high solubility, has not been developed as glycine-site NMDA receptor antagonist having a large affinity for the receptor.

We have now found a novel class of quinolinic sulfide derivatives which are potent and specific antagonists at the strychnine insensitive glycine binding site on the NMDA receptor complex with an pharmacological advantageous profile. They may be useful in treatment or prevention of neurodegenerative disorders. Particularly, the compounds included in the present invention are especially useful for minimizing damage of the central nervous system arising as a consequence of ischemic or hypoxic condition such as stroke, hypoglycemia, cerebral ischemia, cardiac arrest, and physical trauma. They are also useful in prevention of chronic neurodegenerative disorders including epilepsy, Alzheimer's disease, Huntington's disease and Parkinsonism. By virtue of their NMDA receptor antagonist properties, the present compounds may also use as anticonvulsant, analgesic, antidepressant, anxiolytic, and antischizophrenic agent.

SUMMARY OF THE INVENTION

The present invention relates to therapeutically active quinolinic sulfide derivatives acting as potent and specific antagonists of excitatory amino acids, to a process for preparation and to their use in treatment in neurological disorders.

Particularly, the compounds included in the present invention show antagonism toward excitatory action of NMDA receptor, and are especially useful for minimizing damage of the central nervous system arising as a consequence of ischemic or hypoxic condition such as stroke, hypoglycemia, cerebral ischemia, cardiac arrest, and physical trauma.

They are also useful in prevention of chronic neurodegenerative disorders including epilepsy, Alzheiemer's disease, Huntington's disease and Parkinsonism.

By virtue of their NMDA receptor antagonist properties, the present compounds also posses anti-convulsant, analgesic, antidepressant, anxiolytic, and antischizophrenic activities.

DETAILED DESCRIPTION OF THE INVENTION

The present invention relates to active quinolinic sulfide derivatives of formula I and includes all tautomeric forms, a pharmaceutically acceptable salt, and prodrugs thereof;

Formula I

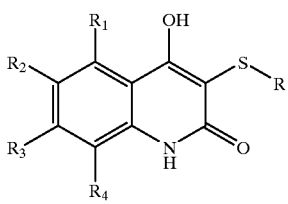

wherein R is a group of aryl of formula II, heterocycles of formula III and formula IV, or substituted-phenyl of formula V:

Formula II

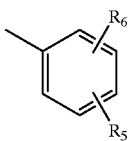

Formula III

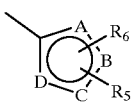

Formula IV

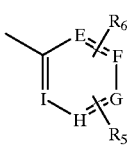

Formula V

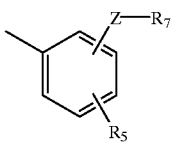

in which closed circle represents two non-adjacent double bonds in any position in five-membered ring of formula III and formula IV;

A, B, C and D independently represent oxygen, sulfur, nitrogen or carbon, provided that at least one of A, B, C and D represents oxygen or sulfur and at least one of A, B, C and D is other than carbon.

E, F, G, H and I independently represent oxygen, sulfur, nitrogen or carbon, provided that at least one of E, F, G, H and I represents oxygen or sulfur and at least one of E, F, G, H and I is other than carbon.

Z represents heteroatom such as nitrogen, oxygen or sulfur atom.

$R_1$, $R_2$, $R_3$ and $R_4$ independently represent hydrogen, hydroxy, halogen, nitro, amino, haloalkyl, cyano, alkyl, alkenyl, alkynyl, azido, acylamino, aryl, alkoxy, or heterocyclic ring.

$R_5$, $R_6$ and $R_7$ independently represents hydrogen, hydroxy, halogen, nitro, amino, carboxylate, thiol, haloalkyl, cyano, alkyl, alkenyl, alkynyl, saturated or unsaturated carbocyclic hydrocarbon, azido, acylamino, sulfonyl, aminosulfonyl, substituted or non-substituted aryl, alkoxy, substituted or non-substituted heterocyclic ring, cyclic amine, acyloxy, alkylthio, arylthio, alkylester, alkylcarboxylate, arylester, arylcarboxylate, aralkylester, aralkylcarboxylate, urea, amidine, aralkyl, heteroarylalkyl, aryl carbonyl, aralkyl carbonyl, alkoxy carbonyl, aralkyloxy carbonyl, aryloxy carbonyl, substituted (halo)-aralkylester, substituted (halo)-arylester, sustituted (halo)-arylsulfonyl, heteroarylcarbonyl, aralkylthiourea, substitued (halo)-arylthiourea, alkoxycarbonyl, iminoalkyl or imonoaralkyi.

Preferred compounds within the scope of Formula I are wherein $R_1$ is hydrogen, nitro, amino, chloro, bromo or alkyl; $R_2$ is hydrogen, chloro, bromo or trifluoromethyl; $R_3$ is nitro, chloro, bromo, trifluoiomethyl or alkyl; $R_4$ is hydrogen, nitro, chloro, bromo or amino; $R_5$ is hyrogen, halogen, nitro, alkyl, amino, hydroxy or alkoxy; $R_6$ is hydrogen, amino, ammonium, hydroxy, halogen, nitro, alkyl, aryl, carboxy, alkylamide, aralainide, aralkylamide or amiroalkyl ; $R_7$ is aralkyl, cyclicamine, alkylamine, substituted or non-substituted heterocyclic ring, heteroarylalkyl, arylcarbonyl, aralkyl carbonyl, alkoxy carbonyl, substituted (halo)-aralkylester, substituted (halo)-arylester, substituted (halo)-arylsulfonyl, heteroarylcarbonyl, aralkylthiourea, substituted (halo)-arylthiourea, iminoalkyl or iminoaryl; and Z is oxygen or nitrogen atom.

Aryl ($C_6$–$C_{14}$) groups contain phenyl, naphthyl, phenanthryl, anthracyl, indenyl, azulenyl, biphenyl, biphenylenyl and fluorenyl groups.

Amino groups are $NH_2$, $NHR_8$ and $NR_8R_9$, wherein $R_8$ and $R_9$ are $C_1$–$C_6$ alkyl groups, preferably $C_1$–$C_4$ alkyl groups.

Halogen atoms are fluorine, chlorine, bromine and iodine.

Alkyl groups are $C_1$–$C_{14}$ alkyl groups, preferably $C_1$–$C_4$ alkyl groups and contain methyl, ethyl, propyl, isopropyl, butyl, sec-butyl, and tert-butyl groups.

Alkenyl groups are $C_2$–$C_{14}$ alkenyl groups, preferably $C_2$–$C_4$ alkenyl groups and contain vinyl, allyl, 1-butenyl, 2-butenyl, 3-butenyl, and isobutenyl groups.

Alkynyl groups are $C_2$–$C_{14}$ alkynyl groups, preferably $C_2$–$C_4$ alkynyl groups and contain propargyl, 1-propynyl, 2-propynyl, 1-butynyl, 2-butynyl and 3-butynyl groups.

Haloalkyl groups are $C_1$–$C_6$ alkyl groups, preferably $C_1$–$C_4$ alkyl groups substituted by one or more fluorine, chlorine, bromine or iodine atoms, and contain fluoromethyl, difluoromethyl, trifluoromethyl groups.

Alkoxy groups contain oxygen substituted by one of $C_1$–$C_{14}$ alkyl groups, preferably $C_1$–$C_4$ alkyl groups.

Heterocyclic groups contain $C_3$–$C_{18}$ heterocycloalkyl, $C_3$–$C_{18}$ heterocycloalkyl($C_1$–$C_6$)alkyl, heteroaryl and heteroaryl($C_1$–$C_6$)alkyl; Suitable heterocycloalkyl groups contain piperidyl, piperazinyl and morpholinyl groups; Suitable heteroaryl groups contain pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl, thiazolyl and thiadiazolyl groups.

For use in medicine, the salts of the compounds of formula I will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formula I include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

The present invention includes within its scope prodrugs of the compounds of formula I. In general, such prodrugs will be functional derivatives of the compounds of formula I which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Particularly preferred compounds of the present invention are selected from a group comprising of:

7-Chloro-4-hydroxy-3-phenylsulfanyl-1H-quinolin-2-one;
7-Chloro-4-hydroxy-3-(3-methoxy-phenylsulfanyl)-1H-quin olin-2-one;
3-(4-Bromo-phenylsulfanyl)-7-chloro-4-hydroxy-1H-quinol in-2-one;
7-Chloro-3-(3,4-dimethyl-phenylsulfanyl)-4-hydroxy-1H-quinolin-2-one;
7-Chloro-4-hydroxy-3-(3-methyl-phenylsulfanyl)-1H-quinolin- 2 one;
7-Chloro-3-(2-chloro-phenylsulfanyl)-4-hydroxy-1H-quinolin-2-one;
7-Chloro-3-(2-carboxy-phenylsulfanyl)-4-hydroxy-1H-quinolin-2on;,
7-Chloro-4-hydroxy-3-(4-methyl-phenylsulfanyl)-1H quinolin-2-one;
7-Chloro-4-hydroxy-3-(2-methyl-phenylsulfanyl)-1H-quinolin-2-one;
3-(3-Bromo-phenylsulfanyl)-7-chloro-4-hydroxy-1H-quinolin-2-one;
3-(2-Bromo-phenylsulfanyl)-7-chloro-4-hydroxy-1H-quinolin-2-one;
7-Chloro-4-hydroxy-3-(4-nitro-phenylsulfanyl)-1H-quinolin-2-one;
7-Chloro-3-(4-hydroxy-phenylsulfanyl)-4-hydroxy-1H-quinolin-2-one;
7-Chloro-4-hydroxy-3-(4-phenylacetylamino-phenylsulfanyl)-1H-quinolin-2-one;
5,7-Dichloro-4-hydroxy-3-(4-methoxy-phenylsulfanyl)-1H-quinolin-2-one;
5,7-Dichloro-4-hydroxy-3-(2-methoxy phenylsulfanyl)-1H-quinolin-2-one;
5,7-Dichloro-4-hydroxy-3-(3-methoxy-phenylsulfanyl)-1H-quinolin-2-one;
5,7-Dichloro-4-hydroxy-3-(2-methoxycarbonyl-phenylsulfanyl)-1H-quinolin-2-one;
3-(2-Carboxy-phenylsulfanyl)-5,7-dlchloro-4-hydroxy-1H-quinolin-2-one;
3-(2-Bomo-phenylsulfanyl)-5,7-dichloro-4-hydroxy-1H-quinolin-2-one;
5,7-Dichloro-4-hydroxy-3-(2-methyl-phenylsulfanyl)-1H-quinolin-2-one;
3-(2-Chloro-phenylsulfanyl)-5,7-dichloro-4-hydroxy-1H-quinolin-2-one;
5,7-Dichloro-4-hydroxy-3-(4-hydroxy-phenylsulfanyl)-1H-quinolin-2-one;
3-(4-Amino-phenylsulfanyl)-5,7-dichloro-4-hydroxy-1H-quinolin-2-one hydrochloride;
3-(Benzothiazole-2-ylsulfanyl)-7-chloro-4-hydroxy-1H-quinolin-2-one;
3-(Benzoxazole-2-ylsulfanyl)-7-chloro-4-hydroxy-1H-quinolin-2-one;
7-Chloro-4-hydroxy-3-(1-methyl-1H-imidazole-2-ylsulfanyl)-1H-quinolin-2-one;
3-(1H-Benzoimidazole-2-ylsulfanyl)-7-chloro-4-hydroxy-1H-quinolin-2-one;
7-Chloro-4-hydroxy-3-(1H-[1.2.4]triazol-3-ylsulfanyl)-1H-quinolin-2-one;
5,7-Dichloro-4-hydroxy-3-(nicotine-2-ylsulfanyl)-1H-quinolin-2-one;
5,7-Dichloro-4-hydroxy-3-(nicotine-6-ylsulfanyl)-1H-quinolin-2-one;
5,7-Dichloro-4-hydroxy-3-(5-N-benzylcarbamoyl-pyridine-2-ylsulfanyl)-1H-quinolin-2-one;
7-Chloro-4-hydroxy-3-(nicotine-2-ylsufanyl)-1H-quinolin-2-one;
5,7-Dichloro-4-hydroxy-3-[1-(4-hydroxy-phenyl)-1H-tetrazole-5-ylsulfanyl]-1H-quinolin-2-one;
5,7-Dichloro-4-hydroxy-3-(1H-[1.2.4]triazole-3-ylsulfanyl)-1H-quinolin-2-one;
3-(4-Benzyloxy-phenylsulfanyl)-5,7-dichloro-4-hydroxy-1H-quinolin-2-one;
5,7-Dichloro-4-hydroxy-3-[4-(piperidin-4-yloxy)-phenylsulfanyl]-1H-quinolin-2-one hydrochloride;
5,7-Dichloro-4-hydroxy-3-[4-(2-piperidin-1-ylethoxy)-phenylsulfanyl]-1H-quinolin-2-one;
5,7-Dichloro-4-hydroxy-3-[4-(2-pyridin-2-ylethoxy)-phenylsulfanyl]-1H-quinolin-2-one;
7-Chloro-4-hydroxy-3-(4-phenylacetylamino-phenylsulfanyl)-1H-quinolin-2-one;
5,7-Dichloro-4-hydroxy-3-(4-phenylacetylamido-phenylsulfanyl)-1H-quinolin-2-one;
3-[4-{2-(3-Bromophenyl)acetamido}-phenylsulfanyl]-5,7-dichloro-4-hydroxy-1H-quinolin-2-one;
3-[4-(3-Chlorophenylamido)-phenylsulfanyl]-5,7-dichloro-4-hydroxy-1H-quinolin-2-one;
3-[4-(4-Chlorophenylsulfonamido)-phenylsulfanyl]-5,7-dichloro-4-hydroxy-1H-quinolin-2-one;
5,7-Dichloro-4-hydroxy-3-[4-(nicotinamido)-phenylsulfanyl]-1H-quinolin-2-one;
5,7-Dichloro-3-[4-(2-furamido)-phenylsulfanyl]-4-hydroxy-1H-quinolin-2-one;
3-(4-Benzylthioureido-phenylsulfanyl)-5,7-dichloro-4-hydroxy-1H-quinolin-2-one;
3-[4-{(3-chlorophenyl)-thioureido}-phenylsulfanyl]-5,7-dichloro-4-hydroxy-1H-quinolin-2-one;
5,7-Dichloro-4-hydroxy-3-[4-(isobutoxy-carbonyl)amino-phenylsulfanyl]-1H-quinolin-2-one;
5,7-Dichloro-3-[4-(4-chloro-benzylamino) phenylsulfanyl]-4-hydroxy-1H-quinolin-2-one hydrochloride;
3-(4-Amino-phenylsulfanyl)-5,7-dichloro-4-hydroxy-1H-quinolin-2-one hydrochloride;
5,7-Dichloro-4-hydroxy-3-[4-(1-imino-ethylamino)-phenylsulfanyl]-1H-quinolin-2-one hydrochloride;
5,7-Dichloro-4-hydroxy-3-{4-[(imino-phenyl-methyl)-amino]-phenylsulfanyl}-1H-quinolin-2-one and pharmaceutically salts and prodrugs thereof.

The pharmaceutical compositions of this invention are preferably in unit dosage forms such as tablets, capsules, powders, granules, sterile solutions or suspensions, or suppositories, for oral, intravenous, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. The liquid forms in which the novel compositions of the present invention may be incorporated for administration orally or by injection include aqueous solutions, suitably, flavoured syrups, aqueous or oil suspensions, and flavoured emulsions with edible oils such as cotton-seed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The present invention also relates process for preparation of the compounds of formula I above.

The compounds of formula I are prepared by the cyclization of formula VI:

Formula VI

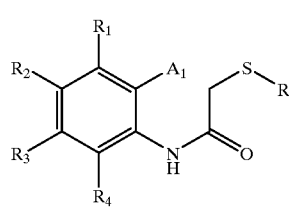

wherein $R_1$, $R_2$, $R_3$, $R_4$ and R are as defined above and $A_1$ represents a reactive carboxylate functionality. The reaction is conveniently carried out in the presence of a base, followed by a mild acidic work-up [J. Heterocycl. Chem. 12, 351 (1975); Bioorg. Med. Chem. Lett. 5, 2643 (1995); J. Med. Chem. 36, 3386 (1993)]. Suitable bases of use in the reaction include sodium, potassium, sodium hydride and potassium hexamethyldisilazide.

Suitable reactive carboxylate functionality $A_1$ includes esters, for example $C_1$–$C_4$ alkyl ester; acid anhydrides, for example mixed anhydrides with $C_1$–$C_4$ alkanoic acids; acid halides, for example acid chlorides; orthoester; and primary, secondary and tertiary amides. Preferably, the group $A_1$ represents methoxycarbonyl or ethoxycarbonyl.

The formula VI above may conveniently be prepared by reacting a compound of formula VII with a compound of formula VIII in case that R is arylthio or heterocycle; and the formula VI may be also prepared by reacting a compound of formula X with a compound of formula XI, wherein the formula X is prepared by reacting a compound of formula VII with a compound of formula IX, in case that R is substituted phenylthio.

Formula VII

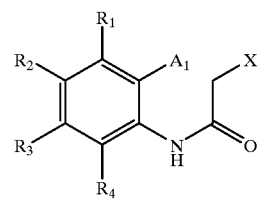

Formula VIII
Formula IX

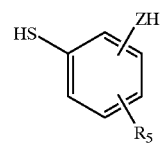

Formula X

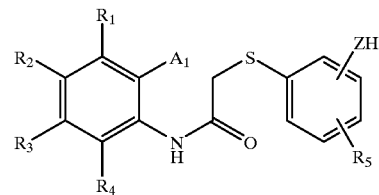

Formula XI

Y—$R_7$ wherein $R_1$, $R_2$, $R_3$, $R_4$, R, $A_1$ and Z are as defined above; X represents halogen atom such as chlorine or bromine atom. The reaction in which the formula VI is prepared by reacting the formula VII with the formula VIII or the formula X is prepared by reacting a compound of formula VII with a compound of formula IX, is conveniently effected by refluxing the reagents and triethyl amine as a mild organic base in an inert solvent, such as tetrahydrofuran, acetonitrile.

Y represents a consumed unit such as chlorine, oxygen atom or hydroxy group in process of the formation of a Z—$R_7$ bond. According to Z of a compound of the formula X, the forming reaction of a Z—$R_7$ bond involves the processes as illustrated in Table I, independently.

TABLE I

Reaction Methods of the Intermediate of Formula X

| Z | Type of Z-R$_7$ bond | Formula XI | Reaction methods |
|---|---|---|---|
| O | ether | alcohols | DEAD, PPh$_3$/THF, rt |
|   |       | halides | ET$_3$N or Na$_2$CO$_3$/THF |
|   | ester | acids | EDC or DCC, DMAP/THF or CH$_2$Cl$_2$ |
|   |       | acid chlorides | Et$_3$N or i-Pr$_2$EtN/THF |
|   | carbonate | carbonate chloroformates | Et$_3$N or i-Pr$_2$EtN/THF or CH$_2$Cl$_2$ |
|   | carbamate | isocyanates carbamoylchlorides | Et$_3$N or i-Pr$_2$EtN/THF or CH$_2$Cl$_2$ |
| N | amide | acid chlorides | Et$_3$N or i-Pr$_2$EtN/THF or CH$_2$Cl$_2$ |
|   |       | acids | EDC or DCC, HOBT/DMF, THF or CH$_2$Cl$_2$ |
|   | sulfonamide | sulfonylchlorides | Et$_3$N or i-Pr$_2$EtN/THF or CH$_2$Cl$_2$ |
|   | urea | isocyanates carbamoylchlorides | Et$_3$N or i-Pr$_2$EtN/THF or CH$_2$Cl$_2$ |
|   | thiourea | thioisocyanates | Et$_3$N or i-Pr$_2$EtN/THF or CH$_2$Cl$_2$ |
|   | amine | aldehydes | NaBH$_3$CN/C$_6$H$_6$ |
|   |       | alcohols | DEAD, PPh$_3$/THF, rt |
|   |       | halides | ET$_3$N or Na$_2$CO$_3$/THF |
|   | amidine | imidates | ET$_3$N, THF |
|   |       | nitriles | anhyd. HCl, MeOH or EtOH |
|   | carbamate | chloroformates | Et$_3$N or i-Pr$_2$EtN/THF or CH$_2$Cl$_2$ |

The intermediate of formula VII above may conveniently be prepared by reacting a compound of formula XII with a choroacetyl chloride or bromoacetyl chloride;

Formula XII

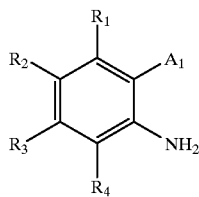

wherein R$_1$, R$_2$, R$_3$, R$_4$, R and A$_1$ are as defined above. The reaction is conveniently effected in an appropriate solvent, such as dichlromethane, 1,2-dichloroethane or tetrahydrofuran at room temperature, inpresence of a mild organic base such as triethyl amine.

The anthranilic acid ester of formula XII and the aromatic thiol of formula VIII and formula IV, where they are not commercially available, may be prepared by the procedure described in the accompanying Examples, or by the analogous procedures for known compounds.

In an alternative process, a compound of formula I may also be prepared by reacting a compound of formula XI with a compound of formula XIII, which is obtained by cyclization of a compound of formula X as described above.

Formula XIII

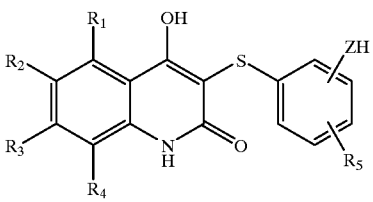

Process for preparation of a compound of formula I may be summarized as following:

b 1) preparing a compound of formula VII by reacting a compound of formula XII with chloroacetyl chloride or bromoacetyl chloride (step I);

b 2) preparing a compound of formula VI by reacting a compound of formula VII with a compound of formula VIII; or by reacting a compound of formula X with a compound of formula XI, wherein the formula X is prepared by reacting a compound of formula VII with a compound of formula IX (step II);

b 3) preparing a compound of formula I by cyclization of a compound of formula VI (step III).

In an alternative process, a compound of formula I is prepared by reacting a compound of formula XI with a compound of formula XIII, which is obtained by cyclization of a compound of formula X.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

INTERMEDIATE 1

N-(3,5-Dichlorophenyl)-2-hydroxyimino-acetamide

A mixture of 3,5-dichloroaniline (10.0 g, 61.7 mmol) in H$_2$O(50 mL), concentrated HCl(12 mL) and 1,4-dioxane (20 mL) was heated to be clear solution, and then added to a mixture of chloral hydrated (10.5 g, 66.9 mmol) and Na$_2$SO$_4$ (66.0 g) in H$_2$O (224 mL) which has been warmed to 50° C. To the above mixture was added hydroxylamine hydrochloride (13.0 g, 180 mmol) in H$_2$O (60 mL), and the mixture was refluxed for 50 mins. After cooling down to room temperature, the insoluble solids was filtered, was washed with excess H$_2$O, and dried in vacuo to provide 12.8 g (89%) of the title compound as a pale yellow solid:

TLC R$_f$=0.5 (EtOAc:n-hexane=1:3); mp 196–197° C.; $^1$H-NMR (DMSO-d$_6$) δ 7.39(t, J=1.8 Hz, 1H, ArH), 7.70(s, 1H, CHNOH), 7.89(d, J=1.8 Hz, 2H, ArH), 10.54(br s, 1H, NH), 12.40(br s, 1H, NOH); MS(EI) m/e 233[M$^+$], 216[M$^+$–OH], 202, 189, 161.

INTERMEDIATE 2

4,6-Dichloro-1H-indole-2,3-dione

The intermediate 1 (10.0 g, 42.9 mmol) was slowly added to concentrated H$_2$SO$_4$ (50 mL) in ice bath. At this moment the reaction mixture should be maintaining below 50° C. After complete addition, the dark solution was heat 90° C. for 10 mins. The resulting mixture was cooled down to room temperature, poured onto 10 times the reaction volume of crushed ice, and the swirled vigorously for 1 hr. The forming insoluble solid was collected, washed with H$_2$O, and dried in vacuo to produce the title compound as an orange colored solid in a 96% (8.90 g) yield :

TLC $R_f$=0.4 (EtOAc:n-hexane=1:3); mp 228–230° C.; $^1$H-NMR (DMSO-$d_6$) δ 6.97(d, J=1.8 Hz, 1H, ArH), 7.32(d, J=1.8 Hz, 1H, ArH), 11.42(br s, 1H, NH); MS(EI) m/e 216[M$^+$], 188[M$^+$–CO], 160.

INTERMEDIATE 3

2-Amino-4,6-dichlorobenzoic acid

To a solution of the intermediate 2 (5.0 g, 23.1 mmol) in 75 mL of 1N NaOH (aq.) was added portionwise a hydrogen peroxide (28% v/v, 10 mL) at room temperature. The mixture was stirred for 2 hrs and was filtered to remove insoluble dark brown solids. The filtrate was cautiously acidified with concentrated HCl at pH 2. The formed yellow precipitates were collected, washed with $H_2O$, and dried in vacuo. After recrystallization from benzene the title compound was obtained as an ivory colored solid in a 82% (3.90 g) yield:

TLC $R_f$=0.1 (EtOAc:n-hexane=1:1); mp 188–189° C.; $^1$H-NMR (DMSO-$d_6$) δ 6.76(d, J=1.9 Hz, 1H, ArH), 6.85(d, J=1.9 Hz, 1H, ArH); MS(EI) m/e 206[M$^+$], 162[M$^+$–$CO_2$].

INTERMEDIATE 4

2-Amino-4,6-dichlorobenzoic acid methyl ester

To a solution of the intermediate 3 (11.5 g, 55.8 mmol) in 20 mL of ethyl ether was added dropwise an ethereal diazomethane solution(prepared from Dazald®) at ice bath temperature. After completed addition, the mixture was warmed up to room temperature, and then was stirred until the intermediate 3 was disappeared. The acetic acid (6.87 mL, 120 mmol) was added to the above mixture to destroy an unreacted diazomethane and the solvent was evaporated under reduced pressure to give a yellow syrup which solidified on standing in vacuo. This provided the title compound (12.1 g, quantitative yield) as a orange colored solid :

$^1$H-NMR (CDCl$_3$) δ 3.88(s, 3H, OCH$_3$), 5.09(br s, 2H, NH$_2$), 6.56(d, J=1.8 Hz, 1H, ArH), 6.73(d, J=1.8 Hz, 1H, ArH); MS(EI) m/e 219[M$^+$–1], 190, 187.

INTERMEDIATE 5

2-Amino-4-chlorobenzoic acid methyl ester

The intermediate 5 was prepared by the same procedure for the intermediate 4, using a commercially available 2-amino-4-chlorobenzoic acid (20.0 g, 116.5 mmol) and an ethereal diazomethane solution. After normal workup, the title compound was obtained as a orange colored solid (21.0 g, 97%):

$^1$H-NMR(CDCl$_3$) δ 3.84(s, 3H, CO$_2$CH$_3$), 5.78(br s, 2H, NH$_2$), 6.57(dd, J$_A$=2.0 Hz, J$_B$=8.6 Hz, 1H, ArH), 6.64(d, J=2.0 Hz, 1H, ArH), 7.75(d, J=8.6 Hz, 1H, ArH); MS(EI) m/e 184[M$_+$], 126.

INTERMEDIATE 6

3,5-Dichloro-2-(2-chloro-acetyl amino)-benzoic acid methyl ester

To a suspension of the intermediate 4 (0.44 g, 2.0 mmol) in anhydrous CH$_2$Cl$_2$ (20 mL) was added Et$_3$N (0.56 mL, 4.0 mmol) and chloroacetyl chloride (0.19 mL, 2.4 mmol). The mixture was stirred at room temperature for 4 hrs under nitrogen atmosphere. After completion of the reaction, the mixture was diluted with 100 mL of methylene chloride, washed with 1N HCl and H$_2$O, and dried over MgSO$_4$. The solvent was removed under reduced pressure to give the crude product. Recrystallization of the above crude product from MeOH provided a white solid the title compound (0.55 g, 93%) as a white solid:

$^1$H NMR(CDCl$_3$) δ 3.99(s, 3H, OCH$_3$), 4.18(s, 2H, COCH$_2$), 7.25(d, J=2.0 Hz, 1H, ArH), 8.38 (d, J=2.0 Hz, 1H, ArH); MS(EI) m/e 295[M$^+$].

INTERMEDIATE 7

4-Chloro-2-(2-chloro-acetyl amino)-benzoic acid methyl ester

The intermediate 7 was prepared by the same procedure for the intermediate 6, using a intermediate 5 (2.7 g, 14.6 mmol), chloroacetyl chloride (2.37 mL, 30.0 mmol) and triethylamine. After normal workup, the pure title compound was obtained by recrystallization from MeOH as a white solid (3.44 g, 90%):

mp 134–135° C.; $^1$H-NMR(CDCl$_3$) δ 3.96(s, 3H, OCH$_3$), 4.22(s, 2H, CH$_2$), 7.13(dd, J=2.1, 6.5 Hz, 1H, ArH), 7.99(d, J=6.5 Hz, 1H, ArH), 8.81(d, J=2.1 Hz, 1H, ArH), 11.92(br s, 1H, NH); MS(EI) m/e 261[M$^+$], 180.

INTERMEDIATE 8

4-Chloro-2-(2-phenylsulfanyl-acetylamino)-benzoic acid methyl ester

To a solution of the intermediate 7 (0.52 g, 2.0 mmol) in THF (15 mL) were added thiophenol (0.22 mL, 2.2 mmol) and triethylamine (0.30 mL, 2.2 mmol). The resulting solution was refluxed for 5 hrs, and washed with 5% NaHCO$_3$ solution. The organic layer was dried over MgSO$_4$, and concentrated. The product was recrystallized from a mixture of ethyl acetate and hexane to give the title compound(0.60 g, 90%) as a white crystal:

mp 99–101° C.; $^1$H NMR(CDCl$_3$) δ 3.79(s, 2H, CH$_2$), 3.89(s, 3H, CO$_2$CH$_3$), 7.04(dd, J=2.0, 8.6 Hz, 1H, ArH), 7.14–7.30(m, 3H, ArH), 7.35–7.41(m, 2H, ArH), 7.91(d, J=8.4 Hz, 1H, ArH), 8.78(d, J=2.2 Hz, 1H, ArH), 11.86(br s, 1H, NH); MS(EI) m/e 337[M$_+$+2], 335[M$_+$], 180, 150, 124.

INTERMEDIATE 9

4-Chloro-2-[2-(3-methoxy-phenylsulfanyl)-acetylamino]-benzoic acid methyl ester

The title compound was prepared by similar procedure for the intermediate 8, and recrystallized from a mixture of ethyl acetate and hexane: 98%, a white solid;

mp 72–73° C.; $^1$H NMR(CDCl$_3$) δ 3.77(s, 3H, OCH$_3$), 3.83(s, 2H, CH$_2$), 3.93(s, 3H, CO$_2$CH$_3$), 6.72–6.77(m, 1H, ArH), 6.98–7.08(m, 3H, ArH), 7.16–7.24(m, 1H, ArH), 7.93(d, J=8.6 Hz, 1H, ArH), 8.81(d, J=2.0 Hz, 1H, ArH), 11.87(s, 1H, NH); MS(EI) m/e 367[M$^+$+2], 365[M$^+$], 180, 124.

INTERMEDIATE 10

2-[2-(4-Bromo-phenylsufanyl)-acetylamino]-4-chlorobenzoic acid methyl ester

The title compound was prepared by similar procedure for the intermediate 8, and recrystallized from a mixture of ethyl acetate and hexane: 95%, a white solid;

mp 98–100° C.; $^1$H NMR(CDCl$_3$) δ 3.76 (s, 2H, CH$_2$), 3.91(s, 3H, CO$_2$CH$_3$), 7.06(dd, J=2.2, 8.4 Hz, 1H, ArH), 7.24–7.35(m, 2H, ArH), 7.36–7.41(m, 2H, ArH), 7.93(d, J=8.6 Hz, 1H, ArH), 8.77(d, J=2.0 Hz, 1H, ArH), 11.82(br s, 1H, NH).

INTERMEDIATE 11

4-Chloro-2-[2-(3,4-dimethyl-phenylsulfanyl)-acetylamino]-benzoic acid methyl ester The title compound was prepared by similar procedure for the intermediate 8, and recrystallized from a mixture of ethyl acetate and hexane: 79%, a white solid;

mp 90–91° C.; $^1$H NMR(CDCl$_3$) δ 2.19(s, 6H, 2CH$_3$), 3.76 (s, 2H, CH$_2$), 3.93(s, 3H, CO$_2$CH$_3$), 7.01–7.26(m, 4H, ArH), 7.94(d, J=8.6 Hz, 1H, ArH), 8.80(d, J=2.0 Hz, 1H, ArH), 11.84(s, 1H, NH); MS(EI) m/e 365[M$^+$+2], 363[M$^+$], 257, 180.

INTERMEDIATE 12

4-Chloro-2-[2-(3-methyl-phenylsulfanyl)-acetylamino]-benzoic acid methyl ester

The title compound was prepared by similar procedure for the intermediate 8, and recrystallized from a mixture of ethyl acetate and hexane: 98%, a white crystal;

mp 75–77° C.; $^1$H NMR(CDCl$_3$) δ 2.26(s, 3H, CH$_3$), 3.78(s, 2H, CH$_2$), 3.81(s, 3H, CO$_2$CH$_3$), 6.97–7.10(m, 2H, ArH), 7.11–7.25(m, 3H, ArH), 7.92(d, J=8.6 Hz, 1H, ArH), 8.79(d, J=2.2 Hz, 1H, ArH), 11.84(s, 1H, NH); MS(EI) m/e 351[M$_+$+2], 349[M$^+$], 180, 91.

INTERMEDIATE 13

4-Chloro-2-[2-(2-chloro-phenylsulfanyl)-acetylamino]-benzoic acid methyl ester

The title compound was prepared by similar procedure for the intermediate 8, and recrystallized from a mixture of ethyl acetate and hexane: 98%, a white solid;

mp 99–101° C.; $^1$H NMR(CDCl$_3$) δ 3.85(s, 2H, CH$_2$), 3.91(s, 3H, CO$_2$CH$_3$), 7.04–7.26(m, 3H, ArH), 7.32–7.40 (m, 2H, ArH), 7.93(d, J=8.6 Hz, 1H, ArH), 8.77(d, J=2.0 Hz, 1H, ArH), 11.79(br s, 1H, NH); MS(EI) m/e 370[M$^+$], 334, 180, 108.

INTERMEDIATE 14

2-[2-(2-Carboxy-phenylsulfanyl)-acetylamino]-4-chlorobenzoic acid methyl ester

The title compound was prepared by similar procedure for the intermediate 8, and recrystallized from a mixture of ethyl acetate and hexane: 88%, a gray solid;

mp 207–209° C.; $^1$H NMR(CDCl$_3$+DMSO-d$_6$) δ 3.86(s, 3H, CO$_2$CH$_3$), 3.93(s, 2H, CH$_2$), 7.09–7.20(m, 2H, ArH), 7.24–7.47 (m, 2H, ArH), 7.91–7.99(m, 2H, ArH), 8.66(d, J=2.0 Hz, 1H, ArH), 11.60(s, 1H, NH); MS(EI) m/e 381 [M$^+$+2], 379[M$^+$], 185, 180.

INTERMEDIATE 15

4-Chloro-2-[2-(4-methyl-phenylsulfanyl)-acetylamino]-benzoic acid methyl ester

The title compound was prepared by similar procedure for the intermediate 8, and recrystallized from a mixture of ethyl acetate and hexane: 99%, a white solid;

mp 91–93° C.; $^1$H NMR (CDCl$_3$) δ 2.27(s, 3H, CH$_3$), 3.74(s, 2H, CH$_2$), 3.91(s, 3H, CO$_2$CH$_3$), 7.01–7.15(m, 3H, ArH), 7.24–7.32(m, 2H, ArH), 7.92(d, J=8.6 Hz, 1H, ArH), 8.74(d, J=2.0 Hz, 1H, ArH), 11.84 (br s, 1H, NH); Ms (EI) m/e 351 [M$^+$+2], 349[M$^+$], 180, 164.

INTERMEDIATE 16

4-Chloro-2-[2-(2-methyl-phenylsulfanyl)-acetylamino]-benzoic acid methyl ester

The title compound was prepared by similar procedure for the intermediate 8, and recrystallized from a mixture of ethyl acetate and hexane: 98%, a white solid;

mp 88–89° C.; $^1$H NMR(CDCl$_3$) δ 2.44(s, 3H, CH$_3$), 3.78(s, 2H, CH$_2$), 3.87(s, 3H, CO$_2$CH$_3$), 7.01–7.18(m, 4H, ArH), 7.24–7.29(m, 1H, ArH), 7.90(d, J=8.6 Hz, 1H, ArH), 8.78(d, J=2.0 Hz, 1H, ArH), 11.80(s, 1H, NH); MS(EI) m/e 351[M$^{30}$ +2], 349[M$^+$], 180, 164.

INTERMEDIATE 17

2-[2-(3-Bromo-phenylsulfanyl)-acetylamino]-4-chlorobenzoic acid methyl ester

The title compound was prepared by similar procedure for the intermediate 8, and recrystallized from a mixture of ethyl acetate and hexane: 99%, a white solid;

mp 89–90° C.; $^1$H NMR(CDCl$_3$) δ 3.82(s, 2H, CH$_2$), 3.95(s, 3H, CO$_2$CH$_3$), 7.09(dd, J=2.2, 8.6 Hz, 1H, ArH), 7.17(d, J=8.6 Hz, 1H, ArH), 7.34–7.39(m, 2H, ArH), 7.60 (s, 1H, ArH), 7.95(d, J=8.6 Hz, 1H, ArH), 8.80(d, J=2.0 Hz, 1H, ArH), 11.86(br s, 1H, NH); MS(EI) m/e 414[M$^+$], 185, 180.

INTERMEDIATE 18

2-[2-(2-Bromo-phenylsulfanyl)-acetylamino]-4-chlorobenzoic acid methyl ester

The title compound was prepared by similar procedure for the intermediate 8, and recrystallized from a mixture of ethyl acetate and hexane: 93%, a white solid;

mp 99–101° C.; $^1$H NMR(CDCl$_3$) δ 3.86(s, 2H, CH$_2$), 3.92 (s, 3H, CO$_2$CH$_3$), 7.02–7.11(m, 2H, ArH), 7.22–7.36 (m, 2H, ArH), 7.56(d, J=9.0 Hz, 1H, ArH), 7.93(d, J=8.6 Hz, 1H, ArH), 8.78 (d, J=2.0 Hz, 1H, ArH) 11.80 (br s, 1H, NH); MS(EI) m/e 415[M$^+$+1], 334, 185, 180.

INTERMEDIATE 19

4-Chloro-2-[2-(4-nitro-phenylsulfanyl)-acetylamino]-benzoic acid methyl ester

The title compound was prepared by similar procedure for the intermediate 8, and recrystallized from a mixture of ethyl acetate and hexane: 95%, a yellowish solid;

mp 134–137° C.; $^1$H NMR(CDCl$_3$) δ 3.89(s, 3H, CO$_2$CH$_3$), 3.92(s, 2H, CH$_2$), 708(dd, J=2.2, 8.6 Hz, 1H, ArH), 7.43–7.49(m, 2H, ArH), 7.93 (d, J=8.6 Hz, 1H, ArH), 8.11–8.17(m, 2H, ArH), 8.77(d, J=2.0 Hz, 1H, ArH), 11.88 (s, 1H, NH); MS(EI) m/e 382[M$^+$+2], 380[M$^+$], 308, 180.

INTERMEDIATE 20

4-Chloro-2-[2-(4-hydroxy-phenylsulfanyl)-acetylamino]-benzoic acid methyl ester

The title compound was prepared by similar procedure for the intermediate 8, and recrystallized from a mixture of ethyl acetate and hexane: 88%, a white solid;

mp 165–168° C.; $^1$H NMR(CDCl$_3$+Acetone-d$_6$) δ 3.71(s, 2H, CH$_2$), 3.98(s, 3H, CO$_2$CH$_3$), 6.77–6.84(m, 2H, ArH), 7.11(dd, J=2.0, 8.6 Hz, 1H, ArH), 7.34–7.41(m, 2H, ArH), 8.01(d, J=8.6 Hz, 1H, ArH), 8.35(s, 1H, OH), 8.81(d, J=2.0 Hz, 1H, ArH), 11.77 (br s, 1H, NH); MS(EI) m/e 353[M$^+$+2], 351[M$^+$], 212, 180, 140.

INTERMEDIATE 21

2-[2-(4-Amino-phenylsulfanyl)-acetylamino]-4-chlorobenzoic acid methyl ester

The title compound was prepared by similar procedure for the intermediate 8, and purified by flash chromatography (n-hexane:EtOAc=5:1): 18%, a gray solid;

mp 145–147° C.; $^1$H NMR(Acetone-d$_6$) δ 3.66(s, 2H, CH$_2$), 3.95 (s, 3H, CO$_2$CH$_3$), 4.82(br s, 2H, NH$_2$), 6.55–6.61 (m, 2H, ArH), 7.14–7.25(m, 3H, ArH), 8.02(d, J=8.6 Hz, 1H, ArH), 8.80(d, J=2.0 Hz, 1H, ArH), 11.68(br s, 1H, NH); MS(EI) m/e 353[M$^+$+2], 351[M$^+$], 180, 125.

INTERMEDIATE 22

4-Chloro-2-[2-(4-phenylacetylamino-phenylsulfanyl)-acetylamino]-benzoic acid methyl ester To a solution of the intermediate 20 (0.35 g, 1.00 mmol) in dry THF (10 mL) was added phenylacetyl chloride (0.15 mL, 1.20 mmol). After 12h, the reaction mixture was washed with 5% NaHCO$_3$ solution, dried over MgSO$_4$, and concentrated. The crude product was purified by flash chromatography (n-hexane:EtOAc=5:1) to give the title compound (0.38 g, 82%) as a white solid:

mp 144–146° C.; $^1$H NMR (CDCl$_3$) δ 3.72 (s, 2H, CH$_2$), 3.74(s, 2H$_1$, CH$_2$), 3.93 (s, 3H, CO$_2$CH$_3$), 7.08(dd, J=2.0, 8.4 Hz, 1H, ArH), 7.27–7.43(m, 9H, ArH), 7.95(d, J=8.6 Hz, 1H, ArH), 8.78(d, J=2.0 Hz, 1H, ArH), 11.87(s, 1H, NH); MS(EI) m/e 469[M$^+$], 180, 91.

INTERMEDIATE 23

2,4-Dichloro-6-[2-(4-methoxy-phenylsulfanyl)-acetylamin o]-benzoic acid methyl ester The reaction was carried out under the similar procedure for the intermediate 8, except use of the intermediate 6, instead the intermediate 7,4-methoxythiophenol and triethylamine in anhydrous THF. After concentration of the solvent and purification by a flash chromatography (n-hexane:EtOAc=4:1), the pure title compound was obtained as a white solid (58%):

mp 78–79° C.; $^1$H NMR (CDCl$_3$) δ 3.65(s, 2H, CH$_2$), 3.76 (s, 3H, OCH$_3$), 3.93 (s, 3H, OCH$_3$), 6.83 (m, 2H, ArH), 7.18 (d, J=2.0 Hz, 1H, ArH), 7.34(m, 2H, ArH), 8.35(d, J=2.0 Hz, ArH), 9.02 (br s, 1H, NH); MS(EI) m/e 400[M$^+$], 180, 135.

INTERMEDIATE 24

2,4-Dichloro-6-[2-(2-methoxy-phenylsulfanyl)-acetylamin o]-benzoic acid methyl ester The title compound was prepared by similar procedure for the intermediate 22, and recrystallized from a mixture of ethyl acetate and hexane: 98%, a white solid;

mp 93–94° C.; $^1$H NMR (CDCl$_3$) δ 3.70 (s, 2H, COCH$_2$S) 3.84 (s, 3H, ArOCH$_3$), 3.85(s, 3H, CO$_2$CH$_3$), 6.88 (m, 2H, ArH), 7.21(m, 3H, ArH), 8.29(d, 1H, J=2.0 Hz, ArH), 10.12 (s, 1H, NH); MS m/e 401[M$^+$], 219[M$^+$–Ph(OCH$_3$)SCH$_2$CO].

INTERMEDIATE 25

2,4-Dichloro-6-[2-(3-methoxy-phenylsulfanyl)-acetylamin o]-benzoic acid methyl ester The title compound was prepared by similar procedure for the intermediate 22, and recrystallized from a mixture of ethyl acetate and hexane: 92%, a white solid;

mp 89–90° C.; $^1$H NMR (CDCl$_3$) δ 3.78(s, 5H, ArOCH$_3$ & COCH$_2$S), 3.86(s, 3H, CO$_2$CH$_3$), 6.70–6.92(m, 3H, ArH), 7.18–7.22 (m, 2H, ArH), 8.37(d, J=2.0 Hz, 1H, ArH), 10.95(br s, 1H, NH); MS m/e 401[M$^+$], 247[M$^+$–CH$_2$SPhOCH$_3$], 219[M$^+$–COCH$_2$SPhOCH$_3$].

INTERMEDIATE 26

2,4-Dichloro-6-[2-(2-methoxy-phenylsulfanyl)-acetylamin o]-benzoic acid methyl ester The title compound was prepared by similar procedure for the intermediate 22, and recrystallized from ethyl acetate: 73%, a pale yellow solid;

mp 150–151° C.; $^1$H NMR (DMSO-d$_3$) δ 3.79(s, 3H, CO$_2$CH$_3$), 3.88(s, 3H, CO$_2$CH$_3$), 3.96(s, 2H, COCH$_2$SPh), 7.30–7.47(m, 1H, ArH), 7.51–7.68(m, 4H, ArH), 7.93–7.96 (m, 1H, ArH), 10.31(s, 1H, NH); MS m/e 429[M$^+$].

INTERMEDIATE 27

2,4-Dichloro-6-[2-(2-carboxy-phenylsulfanyl)-acetylamin o]-benzoic acid methyl ester The title compound was prepared by similar procedure for the intermediate 22, and recrystallized from methanol: 67%, a white solid;

mp 165–166° C.; $^1$H NMR (DMSO-d$_6$) δ 3.76(s, 3H, CO$_2$CH$_3$), 3.89(s, 2H, COCH$_2$S), 7.21–7.28(m, 1H, ArH), 7.41–7.66(m, 4H, ArH), 7.92(d, J=7.8 Hz, ArH), 10.23(s, 1H, NH).

INTERMEDIATE 28

2,4-Dichloro-6-[2-(2-bromo-phenylsulfanyl)-acetylaminol]-benzoic acid methyl ester The title compound was prepared by similar procedure for the intermediate 22, and recrystallized from methanol: 74%, a white solid;

mp 101–102° C.; $^1$H NMR (CDCl$_3$) δ 3.80(s, 2H, COCH$_2$S), 3.81 (S, 3H, CO$_2$CH$_3$), 7.08–7.27(m, 4H, ArH), 7.57(d, J=9.0 Hz, ArH), 8.32(d, J=2.0 Hz, 1H, ArH), 10.07(s, 1H, NH); MS(EI) m/e 371[M$^+$+Br], 340[M$^+$–Br, OCH$_3$].

INTERMEDIATE 29

2,4-Dichloro-6-[2-(2-methyl-phenylsulfanyl)-acetylamino]-benzoic acid methyl ester The title compound was prepared by similar procedure for the intermediate 22, and recrystallized from methanol: 92%, a white solid;

mp 93–94° C.; $^1$H NMR (CDCl$_3$) δ 2.29(σ, 3H, ArCH$_3$), 3.75 (s, 3H, CO$_2$CH$_3$), 3.85(s, 2H, COCH$_2$S), 7.13–7.28(m, 4H, ArH), 7.56(d, J=2.0 Hz, ArH), 7.62(d, J=2.0 Hz, 1H, ArH), 10.16(s, 1H, NH); MS(EI) m/e 384[M$^+$], 352[M$^+$–OCH$_3$].

INTERMEDIATE 30

2,4-Dichloro-6-[2-(2-chloro-phenylsulfanyl)-acetylamino ]-benzoic acid methyl ester The title compound was prepared by similar procedure for the intermediate 22, and recrystallized from methanol: 81%, a white solid;

mp 98–99° C.; $^1$H NMR (CDCl$_3$) δ 3.83(s, 2H, COCH$_2$S), 3.84(s, 3H, CO$_2$CH$_3$), 7.15–7.28(m, 4H, ArH), 7.42–7.39

(m, 1H, ArH), 8.34(d, J=2.0 Hz, 1H, ArH), 10.10(s, 1H, NH); MS(EI) m/e 405[M⁺], 374[M⁺–OCH₃], 369[M⁺–Cl].

INTERMEDIATE 31

2,4-Dichloro-6-[2-(4-hydroxy-phenylsulfanyl)-acetylamin o]-benzoic acid methyl eater The title compound was prepared by similar procedure for the intermediate 22, and recrystallized from a mixture of ethyl acetate and hexane (1:7): 95%, a gray solid;

mp 149–151° C.; ¹H NMR (CDCl₃) δ 3.67(s, 2H, CH₂), 3.96 (s, 3H, CO₂CH₃), 6.70–6.77(m, 2H, ArH), 7.22–7.33 (m, 3H, ArH), 8.34(d, J=2.0 Hz, 1H, ArH), 10.21(s, 1H, NH); MS(EI) m/e 386[M⁺], 214, 166, 47.

INTERMEDIATE 32

6-[2-(4-Amino-phenylsulfanyl)-acetylamino]-2,4-dichloro-benzoic acid methyl ester The title compound was prepared by similar procedure for the intermediate 22, and recrystallized from ethyl acetate and hexane (1:5): 95%, a white solid;

mp 114–116° C.; ¹H NMR (CDCl₃) δ 3.62(s, 2H, CH₂), 3.70–3.83(s, 2H, NH₂), 3.98 (s, 3H, CO₂CH₃), 6.60(dd, J=2.0, 8.4 Hz, 2H, ArH), 7.20–7.26 (m, 3H, ArH), 8.38 (d, J=2.0 Hz, 1H, ArH), 10.19(br s, 1H, NH); MS(EI) m/e 385[M⁺], 165, 124.

INTERMEDIATE 33

2-[2-(Benzothiazole-2-ylsulfanyl)-acetylamino]-4-chloro-benzoic acid methyl ester To a solution of the intermediate 7 (0.52 g, 2.00 mmol) in THF (15 mL) were added a 2-mercaptobenzothiazole (0.37 g, 2.20 mmol) and a triethylamine (0.30 mL, 2.20 mmol). The resulting solution was refluxed for 5h, and washed with 5% NaHCO₃, solution. The organic layer was dried over MgSO₄, and concentrated. The product was recrystallized from ethyl acetate and hexane to give the title compound (0.73 g, 90%) as a white solid:

mp 117–120° C.; ¹H-NMR(CDCl₃) δ 3.83(s, 3H, OCH₃) 4.26 (s, 2H, CH₂) 6.99–7.92(m, 6H, ArH), 8.77 (s, 1H, ArH), 11.72(br s, 1H NH); MS(EI) m/e 393[M⁺], 208, 180.

INTERMEDIATE 34

2-[2-(Benzoxazol-2-ylsulfanyl)-acetylamino]-4-chloro-benzoic acid methyl ester

The title compound was obtained as a white solid (0.65 g, 86%) by the same procedure for the intermediate 33, using the intermediate 7 (0.52 g, 2.00 mmol) and 2-mercaptobenzoxazole (0.31 g, 2.00 mmol):

mp 120–122° C.; ¹H-NMR(CDCl₃) δ 3.81(s, 3H, OCH₃) 4.23(s, 2H, CH₂), 7.04–7.63(m, 5H, ArH), 7.90(d, J=8.5 Hz, 1H, ArH), 8.79(d, J=2.0 Hz, 1H, ArH), 11.75(br s, 1H, NH); MS(EI) m/e 376[M⁺], 192, 165.

INTERMEDIATE 35

4-Chloro-2-[2-(1-methyl-1H-imidazol-2-ylsulfanyl)-acetylamino]-benzoic acid methyl ester The title compound was obtained as a white solid (0.70 g, 83%) by the same procedure for the intermediate 33, using the intermediate 7 (0.65 g, 2.50 mmol) and 2-mercapto-1-methyl imidazole (0.28 g, 2.50 mmol):

mp 93–95° C.; ¹H-NMR (CDCl₃) δ 3.67(s, 3H, NCH₃), 3.82 (s, 3H,OCH₃), 4.01(s, 2H, CH₂), 6.91–7.09(m, 3H, ArH), 7.93(d, J=8.5 Hz, 1H, ArH), 8.77(d, J=2.1 Hz, 1H, ArH), 11.57(s, 1H, NH); MS(EI) m/e 339[M⁺], 128, 95.

INTERMEDIATE 36

2-(2-(1H-Benzoimidazol-2-ylsulfanyl)-acetylaminol-4-chloro-benzoic acid methyl ester The title compound was obtained as a white solid (0.98 g, 87%) by the same procedure for the intermediate 33, using the intermediate 7 (0.78 g, 3.00 mmol) and 2-mercaptobenzimidazole (0.50 g, 3.30 mmol):

mp 146–147° C.; ¹H-NMR (DMSO-d₆) δ 3.86(s, 3H, OCH₃), 4.07(s, 2H, CH₂), 7.04–7.57(m, 5H, ArH), 7.91(d, J=8.5 Hz, 1H, ArH), 8.75(d, J=2.1 Hz, 1H, ArH), 11.70 (s, 1H, NH); MS(EI) m/e 375[M⁺], 164.

INTERMEDIATE 37

4-Chloro-2-[2-(1H-[1.2.4]triazol-3-ylsulfanyl)-acetylamino]-benzoic acid methyl ester The title compound was obtained as a white solid (0.92 g, 94%) by the same procedure for the intermediate 33, using the intermediate 7 (0.78 g, 3.00 mmol) and 1H-1.2.4-triazol-3-thiol (0.33 g, 3.26 mmol):

mp 174–175° C.; ¹H-NMR(DMSO-d₆) δ 3.85(s, 3H, OCH₃), 4.07(s, 2H, CH₂), 7.24(d, J=6.5, 2.1 Hz, 1H, ArH), 7.94(d, J=8.5 Hz, 1H, ArH), 8.56(br s, 2H, ArH), 11.35(br s, 1H, NH); MS(EI) m/e 326[M⁺+1], 185, 115.

INTERMEDIATE 38

2-(3,5-Dichloro-2-methoxycarbonyl-phenylcarbamoylmethyl sulfanyl)-nicotinic acid The title compound was obtained as a white solid (1.05 g, 94%) by the same procedure for the intermediate 33, using the intermediate 6(0.80 g, 2.69 mmol) and 2-mercaptonicotinic acid (0.50 g, 2.82 mmol):

mp 160° C.; ¹H-NMR (DMSO-d₆) δ 3.78(s, 3H, CO₂CH₃), 4.01(s, 2H, COCH₂S), 7.28–7.34(m, 1H, ArH), 7.57(s, 1H, ArH), 7.77(s, 1H, ArH), 8.28(d,1H, J=7.8 Hz, 1H, ArH), 8.63 (d, J=4.6 Hz, 1H, ArH), 10.11(s, 1H, NH).

INTERMEDIATE 39

6-(3,5-Dichloro-2-methoxycarbonyl-phenylcarbamoylmethyl sulfanyl)-nicotinic acid The title compound was obtained as a white solid (1.23 g, 88%) by the same procedure for the intermediate 33, using the intermediate 6 (1.00 g, 3.37 mmol) and 6-mercaptonicotinic acid (0.59 g, 90%, tech, 3.54 mmol):

mp 191–193° C.; ¹H-NMR (DMSO-d₆) δ 3.78(s, 3H, CO₂CH₃), 4.19(s, 2H, COCH₂S), 7.53–7.62(m, 2H, ArH), 7.72(d, J=2.2 Hz, 1H, ArH), 8.13(dd, J=2.2, 8.2 Hz, 1H, ArH), 8.94(d, J=2.2 Hz, 1H, ArH), 10.29(s, 1H, NH), 13.4(br s, 1H, COOH); MS(EI) m/e 415[M⁺], 384[M⁺–OCH3], 366.

INTERMEDIATE 40

2-[2-(5-Benzylcarbamoyl-pyridine-2-ylsulfanyl)-acetylamino]-4,6-dichloro-benzoic acid methyl ester To a solution of the intermediate 39 (0.42 g, 1.01 mmol), 1-(3-dimethylaminopropyl)-3-ethylcarbodiimide (0.72 g, 2.02 mmol), and 1-hydroxybentriazole (0.32 g, 2.02 mmol) in THF (30 mL) was added benzylamine (0.26 mL, 2.02 mmol). The resulting mixture was stirred at room temperature for 2 days. The mixture was diluted with EtOAc (50 mL) and washed with 1N HCl (50 mL) and dried of $MgSO_4$. Evaporation in vacuo and flash column chromatography (n-hexane:EtOAc=9:1) gave the title compound (0.31 g, 61%):

mp 270° C. decomp.; $^1$H-NMR (CDCl$_3$) δ 3.78(s, 3H, CO$_2$CH$_3$), 3.98(s, 2H, COCH$_2$S), 4.67(d, J=5.8 Hz, 2H, COCH$_2$NH), 6.43(br s, 1H, CONH), 7.18(d, J=2.0 Hz, 1H, ArH), 7.32–7.41(m, 6H, ArH), 8.02(dd, J=2.0, 8.2 Hz, 1H, ArH), 8.26(d, J=2.2 Hz, 1H, ArH), 8.93(d, J=2.0 Hz, 1H, ArH), 10.07(br s, 1H, NH).

INTERMEDIATE 41

2-(5-Chloro-2-methoxycarbonyl-phenylcarbamoylmethylsulfanyl)-nicotinic acid

The title compound was obtained as a yellow solid (1.13 g, 93%) by the same procedure for the intermediate 33, using the intermediate 7 (0.84 9, 3.21 mmol) and 2-mercaptonicotinic acid (0.51 g, 3.31 mmol):

mp 165–167° C.; $^1$H-NMR (DMSO-d$_6$) δ 3.86(s, 3H, OCH$_3$), 4.02(s, 2H, CH2), 7.10–7.24(m, 2H, ArH), 7.93(d, J=8.6 Hz, 1H, ArH), 8.23–8.67(m, 3H, ArH), 11.44(s, 1H, NH); MS(EI) m/e 196[M$^+$–185], 197, 185, 153.

INTERMEDIATE 42

2,4-Dichloro-6-{2-[1-(4-hydrocxy-phenyl)-1H-tetrazole-5-ylsulfanyl]-acetylamino}-benzoic acid methyl ester The title compound was obtained as a brown solid (1.15 g, 92%) by the same procedure for the intermediate 33, using the intermediate 6 (0.82 g, 2.75 mmol) and 1-(4-hydroxyphenyl)-1H-tetrazole-5-thiol (0.54 g, 2.78 mmol):

mp 59–60° C. decomp.; $^1$H-NMR (CDCl$_3$) δ 4.00(s, 3H, OCH$_3$), 4.16(s, 2H, CH$_2$), 6.99(d, J=8.7 Hz 2H, ArH), 7.22 (d, J=1.9 Hz, 1H, ArH), 7.41(d, J=8.8 Hz, 2H, ArH), 8.30(d, J=1.9 Hz, 1H, ArH).

INTERMEDIATE 43

2,4-Dichloro-6-[2-[1H-[1.2.4]triazole-3-ylsulfanyl]-acetylamino}-benzoic acid methyl ester The title compound was obtained as a white solid (0.68 g, 94%) by the same procedure for the intermediate 33, using the intermediate 6 (0.60 g, 2.02 mmol) and 1H-1.2.4-triazol-3-thiol (0.22 g, 2.18 mmol):

mp 128–129° C.; $^1$H-NMR (CDCl$_3$) δ 3.90(s, 3H, OCH$_3$), 3.92(s, 2H, CH$_2$), 7.21(d, J=1.8 Hz, 1H, ArH), 8.25(br s, 2H, ArH); MS(EI) m/e 360[M$^+$], 218, 115.

INTERMEDIATE 44

2,4-Dichloro-6-[2-(4-hydroxy-phenylsulfanyl)-acetylamino]-benzoic acid methyl ester To a solution of the intermediate 6 (1.48 g, 5.02 mmol) in THF (30 mL) were added 4-hydroxythiophenol (0.69 g, 5.47 mmol) and triethylamine (0.77 mL, 5.50 mmol). The resulting solution was refluxed overnight, and washed with 5% NaHCO$_3$ solution. The organic layer was dried over MgSO4, and concentrated. The product was recrystallized from a mixture of ethyl acetate and n-hexane (1:7) to give the title compound (1.83 g, 95%) as a gray solid:

mp 149–151° C.; $^1$H-NMR(CDCl$_3$) δ 3.67(s, 3H, CH$_2$), 3.96 (s, 2H, CO$_2$CH$_3$), 6.70–6.77(m, 2H, ArH), 7.22–7.33 (m, 3H, ArH), 8.34(d, J=2.0 Hz, 1H, ArH), 10.21(br s, 1H NH); MS(EI) m/e 386[M$^+$], 214, 166, 47.

INTERMEDIATE 45

6-[2-(4-Amino-phenylsulfanyl)-acetylamino]-2,4-dichloro benzoic acid methyl ester The title compound was prepared by similar procedure for the intermediate 44, using the intermediate 6 (0.88 g, 2.99 mmol), 4-aminothiophenol (0.53 g, 4.26 mmol) in acetonitrile (30 mL) and diisopropylethylamine (0.74 mL, 4.26 mmol). After workup, the crude product was recrystallized from ethyl acetate and n-hexane (1:5) to give the title compound (1.10 g, 95%) as a white solid:

mp 114–116° C.; $^1$H-NMR (CDCl$_3$) δ 3.62(s, 2H, CH$_2$), 3.70–3.83 (m, 2H, NH$_2$), 3.98(s, 3H, CO$_2$CH$_3$), 6.60(dd, J=2.0, 8.4 Hz, 2H, ArH), 7.20–7.26(m, 3H, ArH), 8.38(d, J=2.0 Hz, 1H, ArH), 10.19(br s, 1H, NH); MS(EI) m/e 385[M$^+$], 165, 124.

INTERMEDIATE 46

6-[2-(4-Benzyloxy-phenylsulfanyl)-acetylamino]-2,4-dichloro-benzoic acid methyl ester To a stirred solution of the intermediate 44 (0.59 g, 1.52 mmol), benzyl alcohol (0.19 mL, 1.82 mmol), and triphenylphosphine (0.47 g, 1.82 mmol) in THF (10 mL) was added diethylazodicarboxylate (0.28 mL, 1.82 mmol). After the solution was allowed to stand for 12h at room temperature, the solvent was removed in vacuo. The residue was subjected to silica gel column chromatography (n-hexene:EtOAc=15:1) to give the title compound (0.70 g, 98%) as a clear oil:

$^1$H-NMR (CDCl$_3$) δ 3.78(s, 2H, CH$_2$), 3.91(s, 3H, CO$_2$CH$_3$), 5.01(s, 2H, CH$_2$Ph), 7.07–7.47(m, 10H, ArH), 8.36(d, J=2.0 Hz, 1H, ArH), 11.38(s, 1H, NH); MS(EI) m/e 478[M$^+$+2], 476[M$^+$], 91.

INTERMEDIATE 47

2,4-Dichloro-6-{2-[4-(piperidin-4-yloxy)-phenylsulfanyl]-acetylamino}-benzoic acid methyl ester The title compound was prepared by similar procedure for the intermediate 46, using the intermediate 44 (1.93 g, 4.99 mmol), N-(t-butyloxycarbonyl)-4-hyroxypiperidine (1.16 g, 5.76 mmol), triphenylphosphine (1.49 g, 5.76 mmol) and diethylazodicarboxylate (0.89 mL, 5.76 mmol). After tha reaction mixture was concentrated in vacuo, the residue was dissolved in CH$_2$Cl$_2$ (10 mL) and added trifluoroacetic acid (6 mL). After 2 h, the solvent was removed and diluted with ethylacetate. The organic layer was washed with 1M Na$_2$CO$_3$, dried over MgSO$_4$, and concentrated. The crude product was purified by flash chromatography (EtOAc:triethylamine=50:1) to give the title compound (1.14 g, 49%) as a brownish oil:

$^1$H-NMR (CDCl$_3$) δ 1.60–1.76(m, 2H, CH$_2$), 1.96–2.04 (m, 2H, CH$_2$), 2.77–2.87(s, 2H, CH$_2$), 3.10–3.20(m, 2H, CH$_2$), 3.64(s, 2H, CH$_2$), 3.92(s, 3H, CO$_2$CH$_3$), 4.30(m, 1H, CH), 6.78–6.83(m, 2H, ArH), 7.17(d, J=2.0 Hz, 1H, ArH), 7.28(t, 2H, ArH), 8.34(d, J=2.0 Hz, 1H, ArH), 10.17(br, 1H, NH).

INTERMEDIATE 48

2,4-Dichloro-6-{2-[4-(2-piperidin-1-yl-ethoxy)-phenylsulfanyl]-acetylamino}-benzoic acid methyl ester The title compound was prepared by similar procedure for the intermediate 46, using the intermediate 44 (1.16 g, 3.0 mmol), 1-piperidineethanol (0.53 mL, 4.0 mmol), triphenylphosphine (1.05 g, 4.0 mmol) and diethylazodicarboxylate (0.63 mL, 4.0 mmol). The crude product was purified by flash chromatography (EtOAc:triethylamine=50:1) to give the pure title compound (0.94 g, 63%) as a yellow oil:

$^1$H-NMR (CDCl$_3$) δ 1.39–1.62(m, 6H, 3CH$_2$), 2.19–2.34 (m, 2H, CH$_2$), 2.37–2.59(m, 2H, CH$_2$), 2.74(t, 2H, CH$_2$N), 3.31 (s, 2H, CH$_2$), 3.82(s, 3H, CO$_2$CH$_3$), 4.12(m, 2H, OCH$_2$), 6.80 (dd, J=2.0, 6.8 Hz, 2H, ArH), 7.22–7.38(m, 4H, ArH) MS(EI) m/e 497[M$^+$], 251, 111, 98.

INTERMEDIATE 49

2,4-dichloro-6-{2-[4-(2-pyridin-2-yl-ethoxy)-phenylsulfanyl]-acetylamino}-benzoic acid methyl ester The title compound was prepared by similar procedure for the intermediate 46, using the intermediate 44 (0.59 g, 1.52 mmol), 2-(2-hydroxyethyl)pyridine (0.19 mL, 1.82 mmol), triphenylphosphine (0.47 g, 1.82 mmol) and diethylazodicarboxylate (0.28 mL, 1.82 mmol). After the solution had been allowed to stand for 12h at room temperature, the solvent was removed in vacuo. The crude product was purified by flash chromatography (n-hexane: EtOAc=1:1), and recrystallized from ethyl acetate and hexane (1:7) to give the title compound (0.29 g, 40%) as a white crystal:

mp 96–97° C.: $^1$H-NMR (CDCl$_3$) δ 3.24(t, 2H, CH$_2$Pyr.), 3.65(s, 2H, CH$_2$) 3.93(s, 3H, CO$_2$CH$_3$), 4.37(t, 2H, OCH$_2$), 6.84(d, J=1.8, 7.0 Hz, 2H, ArH), 7.14–7.35(m, 5H, ArH), 7.62(m, 1H, ArH), 8.37(d, J=2.0 Hz, 1H, ArH), 8.54(d, J=4.2 Hz, 1H, ArH), 10.19(s, 1H, NH); MS(EI) m/e 493[M$^+$+2], 491[M$^+$], 229.

INTERMEDIATE 50

4-Chloro-2-[2-(4-phenylacetylamino-phenylsulfanyl)-acetylamino]-benzoic acid methyl ester To a solution of the intermediate 45 (1.00 mmol) in dry THF (10 mL) was added phenylacetyl chloride (1.20 mmol). After stirring for 12 h at room temperature, the reaction mixture was washed with 5% NaHCO$_3$ solution, dried over MgSO$_4$, and concentrated under reduced pressure. The crude product was purified by a flash chromatography (n-hexane:EtOAc=5:1) to give the title compound (82%) as a white solid;

mp 144–146° C., $^1$H-NMR(CDCl$_3$) δ 3.72(s, 2H, CH$_2$), 3.74 (s, 2H, CH$_2$), 3.93(s, 3H, CO$_2$CH$_3$), 7.08(d, J=2.0, 8.4 Hz, 1H, ArH), 7.27–7.43(m, 9H, ArH), 7.95(d, J=8.6 Hz, 1H, ArH), 8.78(d, J=2.0 Hz, 1H, ArH), 11.87(s, 1H, NH); MS(EI) m/e 469[M$^+$], 180, 91.

INTERMEDIATE 51

2,4-Dichloro-6-[2-(4-phenylacetylamino-phenylsulfanyl)-acetylamino]-benzoic acid methyl ester To a solution of the intermediate 45 (1.00 mmol) in dry THF (10 mL) was added phenylacetyl chloride (1.20 mmol). After stirring for 12 h at room temperature, the reaction mixture was washed with 5% NaHCO$_3$ solution, dried over MgSO$_4$, and concentrated under reduced pressure. The crude product was purified by recrystallization from ethyl acetate and hexane (1:9) to give the title compound (82%) as a white solid;

mp 156–158° C.; $^1$H-NMR(CDCl$_3$) δ 3.67(s, 2H, CH$_2$), 3.69 (s, 2H, CH$_2$), 3.87(s, 3H, CO$_2$CH$_3$), 7.16–7.18(br d, 2H, ArH), 7.22–7.42(m, 8H, ArH), 8.32(d, J=2.0 Hz, 1H, ArH), 10.15(s, 1H, NH); MS(EI) m/e 505[M$^+$+2], 503[M$^+$], 384, 229, 91.

INTERMEDIATE 52

2-(2-{4-[2-(3-Bromo-phenyl)-acetylamino]-phenylsulfanyl}-acetylamino)-4,6-dichloro-benzoic acid methyl ester The title compound was prepared by the procedure as described intermediate 51, using a 3-bromophenylacetyl chloride, and recrystallized from ethyl acetate and hexane (1:9): 83%, a white solid;

mp 177–180° C.; $^1$H-NMR (CDCl$_3$) δ 3.67(s, 2H, CH$_2$), 3.71 (s, 2H, CH$_2$), 3.89(s, 3H, CO$_2$CH$_3$), 7.17–7.32(m, 5H, ArH), 7.38–7.47(m, 4H, ArH), 8.34(d, J=2.0 Hz, 1H, ArH), 10.20 (s, 1H, NH); MS(EI) m/e 584[M$^+$+2], 582[M$^+$], 384, 124.

INTERMEDIATE 53

2,4-Dichloro-6-{2-[4-(4-chlorobenzenesulfonylamino)-phenylsulfanyl]-acetylamino}-benzoic acid methyl ester The title compound was prepared by the procedure as described intermediate 51, using a 4-chlorobenzenesulfonyl chloride, and purified by a flash chromatography (n-hexane:EtOAc=5:1): 87%, a white solid;

mp 120–123° C.; $^1$H-NMR (CDCl$_3$) δ 3.70(s, 2H, CH$_2$), 3.86 (s, 3H, CO$_2$CH$_3$), 6.96–7.11(m, 2H, ArH), 7.19–7.25 (m, 3H, ArH), 7.33–7.38(m, 2H, ArH), 7.67(d, J=8.6 Hz, 2H, ArH), 8.31(d, J=1.8 Hz, 1H, ArH), 10.16(s, 1H, NH); MS(EI) m/e 562[M$^+$+2], 560[M$^+$], 351, 229, 111.

INTERMEDIATE 54

2,4-Dichloro-6-(2-{4-[(pyridine-3-carbonyl)-amino]-phenylsulfanyl}-acetylamino)-benzoic acid methyl ester The title compound was prepared by the procedure as described intermediate 51, using a nicotinoyl chloride, and recrystallized from ethyl acetate and hexane (1:10): 97%, a yellowish solid;

mp 156–159° C.; $^1$H-NMR (CDCl$_3$+Acetone-d$_6$) δ 3.82 (s, 2H, CH$_2$), 3.94(s, 3H, CO$_2$CH$_3$), 7.24(s, 1H, ArH), 7.38–7.60 (m, 3H, ArH), 7.76–7.82(d, 2H, ArH), 8.28–8.33 (m, 2H, ArH), 8.74–8.77(m, 1H, ArH), 9.17(s, 1H, ArH), 9.68(br s, 1H, NH), 10.11(s, 1H, NH); MS(EI) m/e 491[M$^+$ 30 1], 302, 229, 189, 106.

INTERMEDIATE 55

2,4-Dichloro-6-(2-{4-[(furan-2-carbonyl)-amino]-phenylsulfanyl}-acetylamino)-benzoic acid methyl ester The title compound was prepared by the procedure as described intermediate 51, using a 2-furoyl chloride, and recrystallized from ethyl acetate and hexane (1:10): 52%, a white solid;

mp 133–135° C.; $^1$H-NMR (CDCl$_3$) δ 3.75(s, 2H, CH$_2$), 3.92 (s, 3H, CO$_2$CH$_3$), 6.58(dd, J=2.0, 4.0 Hz, 1H, ArH), 7.20–7.27(m, 3H, ArH), 7.35–7.40(m, 2H, ArH), 7.60–7.67 (m, 2H, ArH), 8.08(br s, 1H, NH), 8.37(d, J=2.0 Hz, 1H, ArH), 10.24(br s, 1H, NH); MS(EI) m/e 481[M$^+$+2], 479 [M$^+$], 230, 95.

INTERMEDIATE 56

2-{2-[4-(3-Benzyl-thioureido)-phenylsulfanyl]-acetylamino}-4,6-dichloro-benzoic acid methyl ester The title compound was prepared by the procedure as described intermediate 50, using a benzyl isocyanate, and purified by flash chromatography (n-hexane:EtOAc=5:1): 78%, an ivory-colored solid;

mp 152–155° C.; $^1$H-NMR(CDCl$_3$) δ 3.76(s, 2H, CH$_2$), 3.82 (s, 3H, CO$_2$CH$_3$), 4.86(d, J=5.4 Hz, 2H, CH$_2$Ph), 6.32(m, 1H, NH), 7.13–7.42(m, 10H, ArH), 7.88(s, 1H, NH), 8.34(d, J=2.0 Hz, 1H, ArH), 10.09(s, 1H, NH); MS(EI) m/e 428[M$^+$–NHCH$_2$Ph], 214, 91, 47.

INTERMEDIATE 57

2,4-Dichloro-6-(2-{4-[3-(3-chloro-phenyl)-thioureido]-phenylsulfanyl}-acetylamino)-benzoic acid methyl ester The title compound was prepared by the procedure as described intermediate 50, using a 3-chloro-phenyl isocyanate, and purified by flash chromatography (n-hexane:EtOAc=5:1): 97%, a white solid;

mp 148–150° C.; $^1$H-NMR (CDCl$_3$) δ 3.76(s, 2H, CH$_2$), 3.87 (s, 3H, CO$_2$CH$_3$), 7.18–7.38(m, 9H, ArH), 7.88(s, 1H, NH), 7.91(s, 1H, NH), 8.31(d, J=2.0 Hz, 1H, ArH), 10.06(s, 1H, NH); MS(EI) m/e 428[M$^+$–NHPhCl], 384, 229.

INTERMEDIATE 58

5,7-Dichloro-6-(2-{4-[(isobutoxy-carbonyl)-amino]-phenylsulfanyl}-acetylamino)-benzoic acid methyl ester The title compound was prepared by the procedure as described intermediate 51, using an isobutyl chloroformate, and recrystallized from ethyl acetate and hexane (1:8): 68%, a white solid;

mp 155–158° C.; $^1$H-NMR (CDCl$_3$) δ 0.98(s, 3H, CH$_3$), 1.03 (s, 3H, CH$_3$), 1.98(m, 1H, CH), 3.63(s, 3H, CO$_2$CH$_3$), 3.71 (s, 2H, CH$_2$), 3.93(d, J=2.0 Hz, 2H, CH$_2$), 7.21–7.42(m, 5H, ArH), 8.27(s, 1H, ArH), 9.72(s, 1H, NH), 10.20(br s, 1H, NH); MS(EI) m/e 487[M$^{30}$+2], 485[M$^+$], 224, 216.

INTERMEDIATE 59

2,4-Dichloro-6-{2-[4-(4-chloro-benzylamino)-phenylsulfanyl]-acetylamino}-benzoic acid methyl ester To a stirred solution of the intermediate 45 (0.77 g, 2.00 mmol) in benzene (20 mL) was added 4-chlorobenzaldehyde (0.35 g, 2.50 mmol). The resulting solution was refluxed for 4 h equipping with Dean-stark apparatus. The solvent was removed, and the residue was dissolved in methanol (10 mL) followed by the addition of NaCNBH$_3$ (0.20 g, 3.00 mmol). After for 12 h, the solvent was removed and diluted with ethyl acetate (100 mL). The resulting mixture was washed with saturated NaHCO$_3$ solution, dried over MgSO$_4$, and concentrated. The crude product was purified by flash chromatography (Hex:EtOAc=15:1), and recrystallized from ethyl acetate and hexane (1:5), afforded the title compound (0.66 g, 65%) as a white solid:

mp 96–98° C.; $^1$H-NMR (CDCl$_3$) δ 3.58(s, 2H, CH$_2$), 3.97 (s, 3H, CO$_2$CH$_3$), 4.24(s, 2H, CH$_2$), 4.37(br, 1H, NH), 6.49 (dd, J=2.0, 8.6 Hz, 2H, ArH), 7.12–7.29(m, 7H, ArH), 8.36 (d, J=1.8 Hz, 1H, ArH), 10.18(s, 1H, NH); MS(EI) m/e 510[M$^+$], 247, 125.

EXAMPLE 1

7-Chloro-4-hydroxy-3-phenylsulfanyl-1H-quinolin-2-one

To a stirred solution of LiHMDS [prepared by treatment of a hexamethyldisilazide (0.97 mL, 4.5 mmol) in a freshly distilled THF (25 mL) with n-BuLi (4.5 mmol) at –78° C. for 1 h] was dropwise added a solution of the intermediate 8 (0.52 g, 1.5 mmol) in a freshly distilled THF (40 mL) at –78° C. The reaction mixture was stirred for 1 h and then slowly warmed to room temperature. After an additional stirring for 4 h and the resulting mixture was treated with trifluoroacetic acid to pH 1–2. The solvent was removed under reduced pressure to give a crude solid. The crude solid was washed with MeOH, afforded the title compound (0.34 g, 87%) as a gray solid:

mp >300° C.; $^1$H NMR (DMSO-d$_6$) δ 7.09–7.16(m, 3H, ArH), 7.20–7.30(m, 3H, ArH), 8.35(d, J=2.0 Hz, 1H, ArH), 7.91(d, J=8.6 Hz, 1H, ArH), 11.40(br s, 1H, OH), 11.69(s, 1H, NH); MS(EI) m/e 305[M$^+$+2], 303[M$^+$], 180, 121.

EXAMPLE 2

7-Chloro-4-hydroxy-3-(3-methoxy-phenylsulfany)-1H-quinolin-2-one

The title compound was prepared by similar procedure for the example 1: 57%, a gray solid;

mp 199–200° C.; $^1$H NMR (DMSO-d$_6$) δ 3.70(s, 3H, OCH$_3$), 6.57–6.75(m, 3H, ArH), 7.14–7.28(m, 2H, ArH), 7.36(d, J=2.0 Hz, 1H, ArH), 7.92(d, J=8.6 Hz, 1H, ArH), 11.69(s, 1H, NH); MS(EI) m/e 335[M$^+$+2], 333[M$^+$], 300, 126, 108.

EXAMPLE 3

3-(4-Bromo-phenylsulfanyl)-7-chloro-4-hydroxy-1H-quinolin-2-one

The title compound was prepared by similar procedure for the example 1: 90%, a white powder;

mp 275–280° C.(decomp.); $^1$H NMR (DMSO-d$_6$) δ 7.05–7.10 (m, 2H, ArH), 7.26(dd, J=2.0, 8.6 Hz, 1H, ArH), 7.36–7.47 (m, 3H, ArH), 7.93(d, J=8.6 Hz, 1H, ArH), 11.72(s, 1H, NH); MS(EI) m/e 384[M$^+$+2], 382[M$^+$], 269, 108.

EXAMPLE 4

7-Chloro-3-(3,4-dimethyl-phenylsulfanyl)-4-hydroxy-1H-quinolin-2-one

The title compound was prepared by similar procedure for the example 1: 59%, a gray solid;

mp 267–268° C.; $^1$H NMR (DMSO-d$_6$) δ 2.11(s, 6H, 2CH$_3$), 6.79–6.84(m, 1H, ArH), 6.93–7.01(m, 2H, ArH); 7.19(d, J=2.0 Hz, 1H, ArH), 7.23(dd, J=2.0, 8.6 Hz, 1H, ArH), 7.31 (d, J=2.0 Hz, 1H, ArH), 7.87(d, J=8.8 Hz, 1H, ArH), 11.22 (br s, 1H, OH), 11.61(s, 1H, NH); MS(EI) m/e 333[M$^+$+2], 331[M$^+$], 298, 106, 91.

EXAMPLE 5

7-Chloro-4-hydroxy-3-(3-methyl-phenylsulfany)-1H-quinolin-2-one

The title compound was prepared by similar procedure for the example 1: 66%, a white powder;

mp 234–236° C.; $^1$H NMR (DMOS-d$_6$) δ 2.20(s, 3H, CH$_3$), 6.84–6.93(m, 3H, ArH), 7.07–7.15(m, 1H, ArH), 7.22(dd, J=2.2, 8.8 Hz, 1H, ArH), 7.32(d, J=2.0 Hz, 1H, ArH), 7.88(d, J=8.8 Hz, 1H, ArH), 11.3(br s, 1H, OH), 11.64(s, 1H, NH); MS(EI) m/e 319[M$^+$+2], 317[M$^+$], 300, 136, 91

EXAMPLE 6

7-Chloro-3-(2-chloro-phenylsulfanyl)-4-hydroxy-1H-quinolin-2-one

The title compound was prepared by similar procedure for the example 1: 84% a white solid;

mp >300° C.; $^1$H NMR (DMSO-d$_6$) δ 6.70–6.75(m, 1H, ArH), 7.07–7.19(m, 2H, ArH), 7.23(dd, J=2.0, 8.6 Hz, 1H, ArH), 7.34(d, J=2.0 Hz, 1H, ArH), 7.40–7.45(m, 1H, ArH), 7.91(d, J=8.6 Hz, 1H, ArH), 11.75(s, 1H, NH); MS(EI) m/e 303[M$^+$−Cl], 302, 126, 108.

EXAMPLE 7

7-Chloro-3-(2-carboxy-phenylsulfanyl)-4-hydroxy-1H-quinolin-2-one

The title compound was prepared by similar procedure for the example 1: 56%, a white solid;

mp >300° C.; $^1$H NMR(DMSO-d$_6$) δ 6.85(d, J=8.2 Hz, 1H, ArH), 7.13–7.38(m, 4H, ArH), 7.88–7.95(m, 2H, ArH), 11.68 (s, 1H, NH); MS(EI) m/e 329[M$^+$−OH], 302[M$^+$−CO$_2$], 152.

EXAMPLE 8

7-Chloro-4-hydroxy-3-(4-methyl-phenylsulfanyl)-1H-quinolin-2-one

The title compound was prepared by similar procedure for the example 1: 65%, a white powder;

mp 245–246° C.; $^1$H NMR (DMSO-d$_6$) δ 2.22(s, 3H, CH$_3$), 7.00–7.19(br s, 4H, ArH), 7.20–7.31(m, 1H, ArH), 7.34(m, 1H, ArH), 7.89(d, J=8.4 Hz, 1H, ArH), 11.64(br s, 1H, NH); MS(EI) m/e 319[M$^+$+2], 317[M$^+$], 180, 154, 135.

EXAMPLE 9

7-Chloro-4-hydroxy-3-(2-methyl-phenylsulfanyl)-1H-quinolin-2-one

The title compound was prepared by similar procedure for the example 1: 90%, a white solid;

mp 296–299° C.; $^1$H NMR (DMSO-d$_6$) δ 2.39(s, 3H, CH$_3$), 6.69(dd, J=3.6, 5.4 Hz, 1H, ArH), 6.69–7.05(m, 2H, ArH), 7.15–7.23(m, 2H, ArH), 7.35(d, J=2.0 Hz, 1H, ArH), 7.91 (d, 8.8 Hz, 1H, ArH), 11.69(s, 1H, NH); MS(EI) m/e 319 [M$^+$+2], 317[M$^+$], 284, 154, 91.

EXAMPLE 10

3-(3-Bromo-phenylsulfanyl)-7-chloro-4-hydroxy-1H-quinolin-2-one

The title compound was prepared by similar procedure for the example 1: 80%, a white solid;

mp 265–268° C.; $^1$H NMR (DMSO-d$_6$) δ 7.10–7.38(m, 6H, ArH), 7.93(d, J=8.6 Hz, 1H, ArH), 10.27(s, 1H, OH), 11.73 (s, 1H, NH); MS(EI) m/e 384[M$^+$+2], 382[M$^+$9, 156, 108.

EXAMPLE 11

3-(2-Bromo-phenylsulfanyl)-7-chloro-4-hydroxy-1H-quinolin-2-one

The title compound was prepared by similar procedure for the example 1: 78%, a white solid;

mp >300° C.; $^1$H NMR (DMSO-d$_6$) δ 6.72(dd, J=1.6, 8.0 Hz, 1H, ArH), 7.01–7.08(m, 1H, ArH), 7.17–7.29(m, 2H, ArH), 7.36(d, J=2.0 Hz, 1H, ArH), 7.60(dd, J=1.6, 7.8 Hz, 1H, ArH), 7.94(d, J=8.8 Hz, 1H, ArH), 11.76(s, 1H, NH); MS(EI) m/e 384[M$^+$+2], 382[M$^+$], 269, 156, 108.

EXAMPLE 12

7-Chloro-4-hydroxy-3-(4-nitro-phenylsulfanyl)-1H-quinolin-2-one

The title compound was prepared by similar procedure for the example 1: 97%, a yellow solid;

mp >300° C.; $^1$H NMR (DMSO-d$_6$) δ 7.24–7.36(m, 4H, ArH), 7.94(d, J=8.8 Hz, 1H, ArH), 8.05–8.11(m, 2H, ArH), 11.79 (s, 1H, NH); MS(EI) m/e 350[M$^+$+2], 348[M$^+$], 284, 182.

EXAMPLE 13

7-Chloro-3-(4-hydroxy-phenylsulfanyl)-4-hydroxy-1H-quinolin-2-one

The title compound was prepared by similar procedure for the example 1: 37%, a gray solid;

mp >300° C.; $^1$H NMR (DMSO-d$_6$) δ 6.68(d, J=8.4 Hz, 2H, ArH), 7.11(d, J=8.8 Hz, 2H, ArH), 7.23(dd, J=2.0, 8.6 Hz, 1H, ArH), 7.31(s, 1H, ArH), 7.88(d, J=8.6 Hz, 1H, ArH), 9.42(br s, 1H, OH), 11.38(br s, 1H, OH), 11.61(s, 1H, NH); MS(EI) m/e 321[M$^+$+2], 319[M$^+$], 180, 94.

EXAMPLE 14

7-Chloro-4-hydroxy-3-(4-phenylacetylamino-phenylsulfanyl)-1H-quinolin-2-one

The title compound was prepared by similar procedure for the example 1: 45%, a brown solid;

mp 283° C. (decomp.); $^1$H NMR (DMSO-d$_6$) δ 3.59(s, 2H, CH$_2$), 7.09 (d, J=8.4 Hz, 1H, ArH), 7.18–7.32(m, 9H, ArH), 7.47(d, 8.6 Hz, 1H, ArH), 7.88(d, J=8.8 Hz, 1H, ArH), 10.14(s, 1H, NH), 11.28(br s, 1H, OH), 11.64(s, 1H, NH); MS(EI) m/e 437[M$^+$], 243, 180, 91.

EXAMPLE 15

5,7-Dichloro-4-hydroxy-3-(4-methoxy-phenylsulfanyl)-1H-quinolin-2-one

The title compound was prepared by similar procedure for the example 1: 78%, a white solid;

mp 280–282° C.; $^1$H NMR (DMSO-d$_6$) δ 3.80(s, 3H, OCH$_3$), 6.96(m, 2H, ArH), 7.34–7.45(m, 4H, ArH), 11.2(br s, 1H, OH), 11.91(s, 1H, NH); MS(EI) m/e 368[M$^+$], 108.

EXAMPLE 16

5,7-Dichloro-4-hydroxy-3-(2-methoxy-phenylsulfanyl)-1H-quinolin-2-one

The title compound was prepared by similar procedure for the example 1: 81%, a white solid;

mp 269–270° C.; $^1$H NMR(DMSO-d$_6$) δ 3.88(s, 3H, OCH$_3$), 6.62–7.18(m, 4H, ArH), 7.35(d, J=2.2 Hz, 1H, ArH), 7.39(d, J=2.2 Hz, 1H, ArH), 11.90(br s, 1H, NH); MS m/e 369[M$^+$], 338[M$^+$−OCH$_3$], 229[M$^+$−SPhOCH$_3$].

EXAMPLE 17

5,7-Dichloro-4-hydroxy-3-(3-methoxy-phenylsulfanyl)-1H-quinolin-2-one

The title compound was prepared by similar procedure for the example 1: 92%, a white solid;

mp 269–270° C.; $^1$H NMR (DMSO-$d_6$) δ 3.75(s, 3H, OCH$_3$), 6.71–6.79(m, 3H, ArH), 7.19–7.27(m, 1H, ArH), 7.38(d, J=2.0 Hz, 1H, ArH), 7.42(d, J=2.0 Hz, 1H, ArH), 11.95(s, 1H, NH); MS m/e 369[M$^+$], 338[M$^+$–OCH$_3$].

EXAMPLE 18

5,7-Dichloro-4-hydroxy-3-(2-methoxycarbonyl-phenylsulfanyl)-1H-quinolin-2-one

The title compound was prepared by similar procedure for the example 1: 68%, a pale yellow solid;

mp 158–160° C; $^1$H NMR (DMSO-$d_6$) δ 3.98(s, 3H, CO$_2$CH$_3$), 7.45–7.52(m, 2H, ArH), 7.55 (d, J=2.0 Hz, 1H, ArH), 7.93(d, J=7.4 Hz, 1H, ArH), 8.15(d, J=8.0 Hz, 1H, ArH), 8.38(d, J=2.0 Hz, 1H, ArH), 10.37(s, 1H, NH); MS(EI) m/e 397[M$^+$], 366[M$_+$–OCH$_3$].

EXAMPLE 19

3-(2-Carboxy-phenylsulfanyl)-5,7-dichloro-4-hydroxy-1H-quinolin-2-one

The title compound was prepared by similar procedure for the example 1: 75%, a white solid;

mp >300° C.; $^1$H NMR (DMSO-$d_6$) δ 6.92(d, J=8.0 Hz, 1H, ArH), 7.18–7.42(m, 4H, ArH), 7.97(d, J=8.0 Hz, 1H, ArH), 11.9(s, 1H, NH); MS(EI) m/e 383[M$^+$].

EXAMPLE 20

3-(2-Bromo-phenylsulfanyl)-5,7-dichloro-4-hydroxy-1H-quinolin-2-one

The title compound was prepared by similar procedure for the example 1: 83%, a white solid;

mp 285–288° C.; $^1$H NMR (DMSO-$d_6$) δ 6.77(d, J=7.8 Hz, 1H, ArH), 7.03–7.11(m, 1H, ArH), 7.19–7.27(m, 1H, ArH), 7.35–7.63(m, 2H, ArH), 7.62(d, J=7.8 Hz, 1H, ArH), 11.94 (s, 1H, NH); MS(EI) m/e 418[M$^+$], 338[M$^+$–Br].

EXAMPLE 21

5,7-Dichloro-4-hydroxy-3-(2-methyl-phenylsulfanyl)- 1H-quinolin-2-one

The title compound was prepared by similar procedure for the example 1: 84%, a slightly yellow solid;

mp >300° C.; $^1$H NMR (DMSO-$d_6$) δ 2.40(s, 3H, ArCH$_3$), 6.69–6.73(m,1H, ArH), 7.02–7.06(m, 2H, ArH), 7.18–7.20 (m, 1H, ArH), 7.34–7.39(m, 2H, ArH), 11.91(s, 1H, NH); MS(EI) m/e 352[M$^+$], 337[M$^+$–CH$_3$].

EXAMPLE 22

3-(2-Chloro-phenylsulfanyl)-5,7-dichloro-4-hydroxy-1H-quinolin-2-one

The title compound was prepared by similar procedure for the example 1: 71%, a white solid;

mp 285–288° C.; $^1$H NMR (DMSO-$d_6$) δ 6.78–6.83(m, 1H, ArH), 7.15–7.19(m, 2H, ArH), 7.35–7.49(m, 3H, ArH), 11.97(s, 1H, NH); MS(EI) m/e 374[M$^+$], 339[M$^+$–Cl].

EXAMPLE 23

5,7-Dichloro-4-hydroxy-3-(4-hydroxy-phenylsulfanyl)-1H-quinolin-2-one

The title compound was prepared by similar procedure for the example 1: 41%, a gray solid;

mp >300° C.; $^1$H NMR (DMSO-$d_6$) δ 6.63–6.69(m, 2H, ArH), 7.12–7.20(m, 2H, ArH), 7.26–7.32(m, 2H, ArH), 9.48(br, 1H, OH), 11.78(s, 1H, NH).

EXAMPLE 24

3-(4-Amino-phenylsulfanyl)-5,7-dichloro-4-hydroxy-1H-quinolin-2-one hydrochloride The title compound was prepared by similar procedure for the example 1 and a subsequent treatment of the residue with 1M HCl in ether: 60%, a gray solid;

mp >300° C.; $^1$H NMR (DMSO-$d_6$) δ 7.33–7.42(m, 2H, ArH), 7.15–7.28(m, 4H, ArH), 1 0.05(br, 1H, OH), 11.93(s, 1H, NH); MS(EI) m/e 353[M$^+$–HCl], 216, 93.

EXAMPLE 25

3-(Benzothiazole-2-ylsulfanyl)-7-chloro-4-hydroxy-1H-quinolin-2-one

To a stirred solution of LiHMDS [prepared by treatment of a hexamethyldisilazide (0.97 mL, 4.50 mmol) in a freshly distilled THF(25 mL) with n-BuLi (4.50 mmol) at −78° C. for 1 h] was dropwise added a solution of the intermediate 33 (0.58 g, 1.48 mmol) in a freshly distilled THF (40 mL) at −78° C. The reaction mixture was stirred for 1 h and then slowly warmed to room temperature. After an additional stirring for 4 h and resulting mixture was treated with trifluoroacetic acid to pH 1–2. The solvent was removed under reduced pressure to give a crude solid. The crude solid was washed with MeOH, afforded the title compound (0.40 g, 75%) as a yellow solid:

mp >270° C.; $^1$H NMR (DMSO-$d_6$) δ 7.27–7.49(m, 4H, ArH), 7.81–8.02(m, 3H, ArH), 11.90(s, 1H, NH); MS(EI) m/e 360 [M$^+$], 179, 167.

EXAMPLE 26

3-(Benzoxazole-2-ylsulfanyl)-7-chloro-4-hydroxy-1H-quinolin-2-one

The title compound was obtained as a brown colored solid (0.23 g, 42%) by the same procedure for the example 25, using the intermediate 34 (0.60 g, 1,60 mmol):

mp >270° C.; $^1$H NMR (DMSO-$d_6$) δ 7.24–7.57(m, 4H, ArH), 7.80–8.02(m, 3H, ArH), 11.83(br s, 1H, NH); MS(EI) m/e 344[M$^+$], 312, 163, 154.

EXAMPLE 27

7-Chloro-4-hydroxy-3-(1-methyl-1H-imidazole-2-ylsulfanyl)-1H-quinolin-2-one

The title compound was obtained as a white solid (0.39 g, 86%) by the same procedure for the example 25, using the intermediate 35 (0.50 g, 1.47 mmol):

mp 232–233° C.; $^1$H NMR (DMSO-$d_6$) δ 3.77(s, 3H, NCH$_3$), 7.09(dd, J=2.0, 6.6 Hz, 1H, ArH), 7.23(d, J=2.0 Hz, 1H, ArH), 7.43(d, J=1.9 Hz, 1H, ArH), 7.58(d, J=1.9 Hz, 1H, ArH), 7.87(d, J=8.5 Hz, 1H, ArH), 11.14(br s, 1H, NH); MS(EI) m/e 307[M$^+$], 154, 126.

EXAMPLE 28

3-(1H-Benzoimidazole-2-ylsulfanyl)-7-chloro-4-hydroxy-1H-quinolin-2-one

The title compound was obtained as a white solid (0.31 g, 52%) by the same procedure for the example 25, using the intermediate 36 (0.65 g, 1.73 mmol):

EXAMPLE 29

7-Chloro-4-hydroxy-3-(1H-[1.2.4]triazol-3-ylsulfanyl)-1H-quinolin-2-one

The title compound was obtained as a white solid (0.35 g, 86%) by the same procedure for the example 25, using the intermediate 37 (0.45 g, 1.38 mmol):

mp >270° C.; $^1$H NMR (DMSO-d$_6$) δ 7.24(dd, J=6.6, 2.0 Hz, 1H, ArH), 7.33(d, J=1.7 Hz, 1H, ArH), 7.90(d, J=8.7 Hz, 1H, ArH), 8.26(s, 1H, ArH), 11.65(s, 1H, NH); MS(EI) m/e 294[M$^+$], 180.

EXAMPLE 30

5,7-Dichloro-4-hydroxy-3-(nicotine-2-ylsulfanyl)-1H-quinolin-2-one

The title compound was obtained as a white solid (0.23 g, 59%) by the same procedure for the example 25, using the intermediate 38 (0.42 g, 1.02 mmol):

mp >270°; $^1$H NMR (DMSO-d$_6$) δ 7.21–7.27(m, 1H, ArH), 7.34–7.37(m, 2H, ArH), 8.25(d, J=8.0 Hz, 11H, ArH), 8.43(d, J=4.8 Hz, 1H, ArH), 11.8(s, 1H, NH).

EXAMPLE 31

5,7-Dichloro-4-hydroxy-3-(nicotine-6-ylsulfanyl)-1H-quinolin-2-one

The title compound was obtained as a white solid (0.23 g, 85%) by the same procedure for the example 25, using the intermediate 39 (0.30 g, 0.72 mmol):

mp 275° C. (decomp.); $^1$H NMR (DMSO-d$_6$) δ 7.36(d, J=2.0 Hz, 1H, ArH), 7.40(d, J=2.2 Hz, 1H, ArH), 8.03(dd, J=2.4, 8.2 Hz, 1H, ArH), 8.84(d, J=1.6 Hz, 1H, ArH), 8.43(d, J=4.8 Hz, 1H, ArH), 11.94(s, 1H, NH).

EXAMPLE 32

5,7-Dichloro-4-hydroxy-3-(5-N-benzylcarbamoyl-pyridine-2-ylsulfanyl)-1H-quinolin-2-one The title compound was obtained as a white solid (0.17 g, 59%) by the same procedure for the example 25, using the intermediate 40 (0.31 g, 0.61 mmol):

mp 280° C. (decomp.); $^1$H NMR (DMSO-d$_6$) δ 4.45(d, J=5.6 Hz, 2H, ArCH$_2$NH), 7.13(d, J=8.2 Hz, 1H, ArH), 7.23–7.37(m, 7H, ArH), 8.01(dd, J=2.2, 8.4 Hz, 1H, ArH), 8.81(d, J=2.2 Hz, 1H, ArH), 9.12(m, 1H, NH), 11.91(s, 1H, NH).

EXAMPLE 33

7-Chloro-4-hydroxy-3-(nicotine-2-ylsulfanyl)-1H-quinolin-2-one

The title compound was obtained as a white solid (0.08 g, 40%) by the same procedure for the example 25, using the intermediate 41 (0.22 g, 0.58 mmol):

mp 254–256° C. (decomp.); $^1$H NMR (DMSO-d$_6$) δ 7.18–7.33 (m, 3H, ArH), 7.87(d, J=8.7 Hz, 1H, ArH), 8.23(d, J=7.5 Hz, 1H, ArH), 8.40(d, J=4.6 Hz, 1H, ArH), 11.56(s, 1H, NH).

EXAMPLE 34

5,7-Dichloro-4-hydroxy-3-[1-(4-hydroxy-phenyl)-1H-tetrazole-5-ylsulfanyl]-1H-quinolin-2-one The title compound was obtained as a white solid (0.52 g, 90%) by the same procedure for the example 25, using the intermediate 42 (0.63 g, 1.38 mmol):

mp 250–252°F; $^1$H NMR (DMSO-d$_6$) δ 6.98(d, J=8.7 Hz, 2H, ArH), 7.33(d, J=1.8 Hz, 1H, ArH), 7.40(d, J=1.9 Hz, 1H, ArH), 7.53(d, J=8.6 Hz, 2H, ArH), 10.28(br s, 1H, OH), 11.94(s, 1H, NH).

EXAMPLE 35

5,7-Dichloro-4-hydroxy-3-(1H-[1.2.4]triazole-3-ylsulfanyl)-1H-quinolin-2-one

The title compound was obtained as a brown solid (0.15 g, 47%) by the same procedure for the example 25, using the intermediate 43 (0.35 g, 0.97 mmol):

mp 260–263° C. (decomp.); $^1$H NMR (DMSO-d$_6$) δ 7.31(s, 1H, ArH), 7.35(s, 1H, ArH), 8.26(br s, 1H, ArH), 11.8(br s, 1H, NH); MS(EI) m/e 328[M$^+$], 296, 188.

EXAMPLE 36

3-(4-Benzyloxy-phenylsulfanyl)-5,7-dichloro-4-hydroxy-1H-quinolin-2-one

To a stirred solution of LiHMDS [prepared by treatment of a hexamethyldisilazide (0.97 mL, 4.50 mmol) in a freshly distilled THF (25 mL) with n-BuLi (4.50 mmol) at −78° C. for 1 h] was dropwise added a solution of the intermediate 46 (0.71 g, 1.50 mmol) in a freshly distilled THF (40 mL) at −78° C. The reaction mixture was stirred for 1 h and then slowly warmed to room temperature. After an additional stirring for 4 h and the resulting mixture was treated with trifluoroacetic acid to pH 1–2. The solvent was removed under reduced pressure to give a crude solid. The crude solid was washed with MeOH, afforded the title compound (0.42 g, 64%) as an ivory colored solid:

mp 224–227° C.; $^1$H NMR (DMSO-d$_6$) δ 5.07(s, 2H, CH$_2$Ph), 6.93–6.99(m, 2H, ArH), 7.21–7.45(m, 9H, ArH), 11.83(s, 1H, NH); MS(EI) m/e 443[M$^+$–H], 354[M$^+$–CH$_2$Ph], 91.

EXAMPLE 37

5,7-Dichloro-4-hydroxy-3-[4-(piperidin-4-yloxy)-phenylsulfanyl]-1H-quinolin-2-one hydrochloride To a stirred solution of LiHMDS [prepared by treatment of a hexamethyldisilazide (1.53 mL, 7.12 mmol) in a freshly distilled THF (30 mL) with n-BuLi (7.12 mmol) at −78° C. for 1 h] was dropwise added a solution of the intermediate 47 (0.84 g, 1.78 mmol) in a freshly distilled THF (50 mL) at −78° C. The reaction mixture was stirred for 1 h and then slowly warmed to room temperature. After an additional stirring for 5 h, the solvent was removed under reduced pressure. The residue was dissolved in methanol (10 mL) and treated with 1 M HCl solution in ether (10 mL). The solvent was evaporated to afford the title compound (0.28 g, 33%) as an ivory colored solid:

mp 286–290° C. (decomp.); $^1$H NMR (DMSO-d$_6$) δ 1.75–1.99 (m, 2H, CH2), 2.03–2.19(m, 2H, CH$_2$), 2.93–3.35 (m, 4H, 2CH$_2$), 4.62(m, 1H, CH), 6.90–7.03(m, 2H, ArH), 7.20–7.32 (m, 2H, ArH), 7.38(br s, 2H, ArH), 9.12(br m, 1H, NH), 11.20(br, 1H, OH), 11.92(s, 1H, NH); MS(EI) m/e 353 [M$^+$–C$_5$H$_{10}$N. HCl], 229, 233.

EXAMPLE 38

5,7-Dichloro-4-hydroxy-3-[4-(2-piperidin-1-yl-ethoxy)-phenylsulfanyl]-1H-quinolin-2-one To a stirred solution of LiHMDS [prepared by treatment of a hexamethyldisilazide (1.20 mL, 5.64 mmol) in a freshly distilled THF (25 mL) with n-BuLi (5.64 mmol) at −78° C. for 1 h] was dropwise added a solution of the intermediate 48 (0.94 g, 1.88 mmol) in a freshly distilled THF (45 mL) at −78° C. The reaction mixture was stirred for 1 h and then slowly warmed to room temperature. After an additional stirring for 5 h, the solvent was removed under reduced pressure. The residue was dissolved in methanol (10 mL) and triturated with hexane to give the title compound (0.21 g, 20%) as a brownish solid;

mp 158–165° C. (decomp.); $^1$H NMR (DMSO-d$_6$) δ 1.32–1.48 (m, 6H, 3CH$_2$), 2.32–2.53(m, 4H, 2CH$_2$), 2.58(t, 2H, CH$_2$N), 3.94(s, 2H, OCH$_2$), 6.61–6.70(br d, 2H, ArH), 6.72–6.86(m, 2H, ArH), 6.98(d, J=1.6 Hz, 1H, ArH), 7.28(d, J=1.6 Hz, ArH).

EXAMPLE 39

5,7-Dichloro-4-hydroxy-3-[4-(2-pyridin-2-yl-ethoxy)-phenylsulfanyl]-1H-quinolin-2-one The title compound was prepared by similar procedure for the example 36, using the intermediate 49: 81%, a yellow solid;

mp u↓300° C.; $^1$H NMR (DMSO-d$_6$) δ 3.12(t, 2H, CH$_2$Pyr.), 4.28(t, 2H, OCH$_2$), 6.62–6.72(br d, 2H, ArH), 6.79–6.88(br d, 1H, ArH), 7.05–7.39(m, 5H, ArH), 7.70(m, 1, ArH), 8.48(m, 1H, ArH), 9.45(s, 1H, OH), 11.76(s, 1H, NH).

EXAMPLE 40

7-Chloro-4-hydroxy-3-(4-phenylacetylamino-phenylsulfanyl)-1H-quinolin-2-one

The title compound was prepared by similar procedure for the example 36, using the intermediate 50: 45%, a brown solid;

mp 283° C. (decomp); $^1$H NMR (DMSO-d$_6$) δ 3.59(s, 2H, CH$_2$), 7.09(d, J=8.4 Hz, 1H, ArH), 7.18–7.32(m, 9H, ArH), 7.47(d, J=8.6 Hz, 1H, ArH), 7.88(d, J=8.8 Hz, 1H, ArH), 10.14(s, 1H, NH), 11.28(br s, 1H, OH), 11.64(s, 1H, NH); MS(EI) m/e 437[M$^+$], 243, 180, 91.

EXAMPLE 41

5,7-Dichloro-4-hydroxy-3-(4-phenylacetylamido-phenylsulfanyl)-1H-quinolin-2-one

The title compound was prepared by similar procedure for the example 36, using the intermediate 51: 67%, an ivory-colored solid;

mp >300° C. $^1$H NMR (DMSO-d$_6$) δ 3.62(s, 2H, CH$_2$), 7.12–7.19 (m, 2H, ArH), 7.22–7.35(m, 7H, ArH), 7.40–7.53 (m, 2H, ArH), 10.16(s, 1H, NH), 11.84(s, 1H, NH); MS(EI) m/e 472 [M$^+$+], 470, 229, 91.

EXAMPLE 42

3-[4-{2-(3-Bromophenyl)acetamido}-phenylsulfanyl]-5,7-dichloro-4-hydroxy-1H-quinolin-2-one The title compound was prepared by similar procedure for the example 36, using the intermediate 52: 97%, an ivory-colored solid;

mp 292–296° C.; $^1$H NMR (DMSO-d$_6$) δ 3.63(s, 2H, CH$_2$), 7.08–7.19(m, 2H, ArH), 7.22–7.39(m, 4H, ArH), 7.40–7.51 (m, 4H, ArH), 10.19(s, 1H, NH), 11.23(br, 1H, OH), 11.85 (s, 1H, NH); MS(EI) m/e 552[M$^+$+2], 550[M$^+$], 321, 229, 125.

EXAMPLE 43

3-[4-(3-Chlorophenylamido)-phenylsulfanyl]-5,7-dichloro-4-hydroxy-1H-quinolin-2-one To a stirred solution of 3-(4-amino-phenylsulfanyl)-5,7-dichloro-4-hydroxy-1H-quinoline-2-one hydrochloride (0.47 g, 1.21 mmol) in THF (5 mL) were added 3-chlorobenzoyl chloride (0.24 mL, 1.5 mmol) and triethylamine (0.25 mL, 1.5 mmol). After being stirred for 12 h, the solvent was removed in vacuo. The formed solid was washed with CHCl$_3$ to give a desired product (32 mg, 5%) as a gray solid:

mp >300° C.; $^1$H NMR (DMSO-d$_6$) δ 7.16–7.23(m, 2H, ArH), 7.32–7.38(m, 2H, ArH), 7.53–7.73(m, 4H, ArH), 7.88–8.03 (m, 2H, ArH), 10.35(s, 1H, NH), 11.87(s, 1H, NH); MS(EI) m/e 492[M$^+$], 230, 139.

EXAMPLE 44

3-[4-(4-Chlorophenylsulfonamido)-phenylsulfanyl]-5,7-dichloro-4-hydroxy-1H-quinolin-2-one The title compound was prepared by similar procedure for the example 36, using the intermediate 53: 41%, a gray solid;

mp 270–274° C.; $^1$H NMR (DMSO-d$_6$) δ 6.96–7.09(m, 3H, ArH), 7.29–7.38(m, 2H, ArH), 7.61–7.77(m, 5H, ArH), 10.34 (s, 1H, NH), 11.86(s, 1H, NH); MS(EI) m/e 322[M$^+$−SO$_2$PhCl], 298, 229, 124.

EXAMPLE 45

5,7-Dichloro-4-hydroxy-3-[4-(nicotinamido)-phenylsulfanyl]-1H-quinolin-2-one

The title compound was prepared by similar procedure for the example 36, using the intermediate 54: 56%, an ivory-colored solid;

mp >300° C.; $^1$H NMR (DMSO-d$_6$) δ 7.15–7.24(m, 2H, ArH), 7.30–7.35(m, 2H, ArH), 7.50–7.57(m, 1H, ArH), 7.61–7.71 (dd, 2H, ArH), 8.23–8.28 (d, 1H, ArH), 8.70–8.76 (m, 1H, ArH), 9.04–9.09(m, 1H, ArH), 10.43(s, 1H, NH), 11.85(s, 1H, NH); MS(EI) m/e 457[M$^+$−1], 230, 106.

EXAMPLE 46

5,7-Dichloro-3-[4-(2-furamido)-phenylsulfanyl]-4-hydroxy-1H-quinolin-2-one

The title compound was prepared by similar procedure for the example 36, using the intermediate 55: 76%, an ivory-colored solid;

mp 296–300° C.; $^1$H NMR (DMSO-d$_6$) δ 6.68(dd, J=2.0, 4.0 Hz, 1H, ArH), 7.07–7.17(m, 2H, ArH), 7.21–7.42(m, 3H, ArH), 7.56–7.66(m, 2H, ArH), 7.88–7.91(m, 1H, ArH), 10.18 (s, 1H, NH), 11.21(br, 1H, OH), 11.85(s, 1H, NH); MS(EI) m/e 449[M$^+$+2], 447[M$^+$], 317, 229, 95.

EXAMPLE 47

3-(4-Benzylthioureido-phenylsulfanyl)-5,7-dichloro-4-hydroxy-1H-quinolin-2-one

The title compound was prepared by similar procedure for the example 36, using the intermediate 56: 86%, a pale-yellow solid;

mp 282° C.; (decomp.); $^1$H NMR (DMSO-d$_6$) δ 4.70(d, J=5.0 Hz, 2H, CH$_2$Ph), 7.07–7.18(m, 3H, ArH), 7.20–7.39 (m, 8H, ArH), 8.15(m, 1H, NH), 9.58(s, 1H, NH), 11.82(s, 1H, NH).

EXAMPLE 48

3-[4-{(3-chlorophenyl)-thioureido}-phenylsulfanyl]-5,7-dichloro-4-hydroxy-1H-quinolin-2-one The title compound was prepared by similar procedure for the example 36, using the intermediate 57: 72%, an ivory-colored solid;

mp ú⌡300° C. (soften at 202° C.); $^1$H NMR (DMSO-d$_6$) δ 7.09–7.19(m, 3H, ArH), 7.21–7.43(m, 6H, ArH), 7.68(s, 1H, ArH), 9.92(s, 1H, NH), 9.94(s, 1H, NH), 11.88(br s, 1H, NH).

EXAMPLE 49

5,7-Dichloro-4-hydroxy-3-[4-(isobutoxy-carbonyl) amino-phenylsulfanyl]-1H-quinolin-2-one The title compound was prepared by similar procedure for the example 36, using the intermediate 58: 47%, a gray solid;

mp >300° C.; $^1$H NMR (DMSO-d$_6$) δ 0.93(s, 3H, CH$_3$), 0.97 (s, 3H, CH$_3$), 1.94(m, 1H, CH), 3.88(d, J=6.0 Hz, 2H, CH$_2$), 7.15–7.19(d, 2H, ArH), 7.36–7.46(m, 4H, ArH), 964 (s, 1H, NH), 11.21(br, 1H, OH), 11.87(s, 1H, ArH); MS(EI) m/e 455[M$^+$+2], 453[M$^+$], 378, 229.

EXAMPLE 50

5,7-Dichloro-3-[4-(4-chloro-benzylamino)-phenylsulfanyl)-4-hydroxy-1H-quinolin-2-one hydrochloride The title compound was prepared by similar procedure for the example 36, using the intermediate 59: 46%, a yellowish solid;

mp 274–278° C.; 1H NMR (DMSO-d$_6$) δ 4.35(s, 2H, CH$_2$Ph), 6.66(d, 2H, ArH), 7.26–7.47(m, 6H, ArH), 7.67–7.71(m, 2H, ArH), 11.90(br s, 1H, ArH); MS(EI) m/e 338[M$^+$–176], 248, 229, 216, 140.

EXAMPLE 51

3-(4-Amino-phenylsulfanyl)-5,7-dichloro-4-hydroxy-1H-quinolin-2-one hydrochloride The title compound was prepared by similar procedure for the example 36 and a subsequent treatment of the residue with 1M HCl in ether: 60%, a gray solid;

mp >300° C.; $^1$H NMR (DMSO-d$_6$) δ 7.33–7.42(m, 2H, ArH), 7.15–7.28(m, 4H, ArH), 10.05(br, 1H, OH), 11.93(s, 1H, NH); MS(EI) m/e 353[M$^+$–HCl], 216, 93.

EXAMPLE 52

5,7-Dichloro-4-hydroxy-3-[4-(1-imino-ethylamino)-phenylsulfanyl]-1H-quinolin-2-one hydrochloride To a stirred solution of the example 51 (0.36 g, 0.9 mmol) in ethanol (5 mL) were added ethyl acetimidate hydrochloride (0.25 mL, 1.8 mmol) and triethylamine (0.27 mL, 1.8 mmol). After being stirred for 12 h at refluxing temperature, the mixture was cooled to 5° C.C., and triturated with 1 M HCl solution in ether (10 mL). The solvent was evaporated to afford the title compound (64 mg, 17%) as a gray solid:

mp ú⌡280° C. (decomp.); $^1$H NMR (DMSO-d$_6$) δ 2.02(s, 3H, CH$_3$), 6.96(m, 1H, NH), 7.11–7.25(m, 2H, ArH$^+$NH), 7.33–7.39(m, 3H, ArH), 7.42–7.53(m, 2H, ArH), 9.97(s, 1H, OH), 11.88(s, 1H, NH); MS(EI) m/e 394[M$^+$–HCl], 230, 124.

EXAMPLE 53

5,7-Dichloro-4-hydroxy-3-{4-[(imino-phenyl-methyl)-amino]-phenylsulfanyl}-1H-quinolin-2-one The title compound was prepared by similar procedure for the example 52, except using a ethyl benzoylimidate hydrochloride: 10%, a gray solid;

mp 245–250° C. (decomp.); $^1$H NMR (DMSO-d$_6$) δ 6.89(s, 1H, ArH), 7.00–7.15(m, 5H, ArH), 7.51–7.75(m, 3H, ArH), 7.84–7.93(m, 2H, ArH), 10.18(s, 1H, NH); MS(EI) m/e 457[M$^+$+1], 352, 229, 103.

I. In Vitro Screening for Binding Activity

1) Synaptic Membrane Preparation

Male Sprague-Dawley rats (300–400 g) were obtained from Experimental Animal Laboratory, Korea Research Institute of Chemical Technology (KRICT), Korea. Animals were housed with water and standard laboratory food freely available, in air-conditioned rooms (22Í⌡1° C.; relative humidity 60Í⌡5%) under a 12-hr light-dark cycle (lights on at 8:00 A.M.), for a period ranging from 4 to 10 days before use. Synaptic membranes for receptor binding were prepared by the modified methods of Foster and Fagg (Eur. J. Pharmacol., 133, 291 (1987)) and Murphy et al. (Br. J. Pharmacol., 95, 932 (1988)). In brief, male Sprague-Dawley rats (300Í400 g) were decapitated, the cerebral cortex and hippocampus were removed chopped with scalpel and homogenized in 10 volumes of 0.32 M sucrose using a Teflon-glass homogenizer by 5 strokes. Following centrifugation at 1,000×g for 10 min in Beckman J2/21 centrifuge (rotor: JA20), the supernatant was collected and centrifugated at 20,000×g for 20 min. The supernatant was discarded, and the pellet homogenizer (setting No. 5, 30 sec).

After incubation at 4° C. for 30 min, the membrane suspension was then centrifugated at 39,000×g for 25 min in Beckman L8-M Ultracentrifuge. The pellet was stored at –70° C. overnight. On the next day, the pellet was thawed at room temperature for 10 min, resuspended with 20 volumes of 50 mM Tris-acetate (pH 7.1 at 4° C.) containing 0.04% Triton X-100, incubated at 37° C. for 20 min, and centrifuged at 39,800×g for 20 min as above. The pellet was washed three times by centrifugation as above with 20 volumes of 50 mM Tris-acetate, pH 7.1, without detergent. The final pellet was suspended in 50 mM Tris-acetate, pH 7.1, and protein concentration was determined using Bio-Rad agent (Bradford, 1976). The resuspending buffer volume was adjusted to give a membrane protein concentration of 1 mg/mL, and aliquots were stored at –70° C.

2) [$^3$H]MDL-105,519 Binding Assay

[$^3$H] MDL 105,519 binding assays were performed in 96-well plates. The synaptic membranes of 50 μg per well used in a final volume of 0.25 mL reaction mixture and incubated at 25° C. for 30 min with 50 mM Tris-acetate buffer, pH 7.1. For drug displacement analysis, various concentrations of testing compounds were incubated as described above, in a reaction mixture containing 4 nM of [$^3$H] MDL 105,519. After incubation, the reaction was terminated by the rapid filtration of the reaction mixture and washed 9 times with 200 mL of ice-cold 50 mM Tris-acetate buffer using a Inotech harvester (Inotech, Switzerland) by rapid filtration through Wallac GF/A glass fiber filter (Wallac, Finland) which was presoaked in assay buffer. The trapped radioactivity on the filter was measured by the plate counter (Wallac Microbeta) at a counting efficiency of 30–40%. Non-specific binding was determined in the presence of 1 mM glycine. All testing compounds were dissolved in dimethylsulfoxide (DMSO), and serially diluted to various concentrations for binding assays.

3) [$^3$H]MK-801 Binding Assay

[$^3$H]MK-801 binding assays were carried out as described by Wong et al. (J.Neurochem., 50, 274 (1988)). For saturation binding analysis of [$^3$H]MK-801, synaptic membranes (300 μg of membrane protein) were incubated at 30° C. for 60 min in final volume of 1 mL reaction mixture containing 50 mM Tris-acetate, pH 7.1, 0.1 2–250 nM [$^3$H]MK-801 in either the presence or the absence of 0.1 μM L-glutamate and 1 μM glycine for drug displacement analysis, synaptic membranes (200l300 μg of membrane protein) were incubated above, in a reaction mixture containing 50 mM Tris-acetate buffer, pH 7.1, 5 nM [$^3$H] MK-801 and various concentrations of testing compound. The reaction was terminated, filtered, and counted as described for [$^3$H] glycine binding assays. Non-specific was determined in presence of 0.1 mM (+)MK-801.

II. In Vivo Screening for Anticonvulsive Activity

1) NMDA (i.c.v.)-Induced Convulsion Test

Based on the Chugai's method, dose-effect curves were established for convulsion induced by i.c.v. administration of NMDA (40 ngĺ; 160 ng/mouse). A 28 gauge injection needle attached to 50μl syringe was inserted through the soft bone 1 mm to the right of bregma on the coronal suture, and testing solution was injected using Manipulator. The injection volume was 5μl/mouse. The convulsive response to NMDA began within 5 min and consisted of 1) wild running or jumping, 2) myoclonic seizures (i.e., isolated, jerky limb movements) and 3) clonic seizures (i.e., repetitive movements involving all limbs simultaneously loss of righting). The animal was observed for 10 min after i.c.v. injection and was scored as showing seizure activity when clonic seizure was present. To examine NMDA-antagonist properties of test drugs, the following procedure was used. Fifteen minutes after the i.p. injection of a test drug (injection volume, 1 mL/100 g), mice were injected with 160 ng of NMDA in 5 μl/mouse. For the examination by i.c.v. administration, the test drug and NMDA solution was simultaneously injected. Each drug dose was tested in ten mice. Test drug dose were increased until a dose was reached that antagonized NMDA (Korea and Colpaert, 1990). NMDA was dissolved in 0.9% sodium chloride solution. AP5, 5,7-dichlorokynurenic acid and 7-chlorokynurenic acid was dissolved in minimum quantity of 0.1N NaOH, to which 0.9% saline was added.

2) Permanent Occlusion of Middle Cerebral Artery (MCA)

MCA occlusion was performed according to the method of Nagfuji et al. (Neurosci. Lett. 147, 159 (1992), Mol. Chem. Neuropathol. 26, 107 (1995), NeuroReport 6, 1541 (1995)). In brief, male SD rats (300–350 g) were anesthetized with 2% halothane for induction and 1.5% halothane for maintenance in nitrous oxide:oxygen (70:30) using halothane vaporizer. After placing the animal on its side position, the left temporalis muscle was incised and the zygomatic arch were partly divided using a bi-polar coagulator. A tiny craniectomy was performed with a microdrill cooled with cold saline just anterior to the foramen of the mandibular nerve under an operating microscope. The inner margin of the olfactory nerve and the main trunk of MCA were seen through the thin dura mater. The MCA trunk proximal to the lenticulostriate artery (arteries) (LSA) was exposed and occluded using a miniclip. The MCA trunk and the LSAs distal to the miniclip were cauterized using a bipolar coagulator. During the surgery, the temperature in the right temporalis muscle and the rectum was kept constant at around 37° C. using a heating pad. The retracted temporalis muscle was allowed to fall back into place and sutured. The animals were placed in the cage and kept warm using a heating lamp overnight. After 24 hours of MCA occlusion, the animals were decapitated and brains were removed quickly, soaked in cold saline shortly, and sliced coronally with the interval of 2 mm from the frotal pole. The slices were incubated in 2% TTC solution, prepared fresh in saline and prewarmed to 37° C., for 30 min at 37° C. The strained slices were fixed in 4% formalin solution. The infarct area in each slice were measured by image analyzer using a stereomicroscope. The infarct size in the left hemisphere was determined by subtracting non-infarct size in the left hemisphere from that in the right hemisphere to exclude the influence the influence of edema formation.

Effect of the Invention

A class of quinolinic sulfide derivatives of the present invention are potent and specific antagonists at the strychnine insensitive glycine binding site on the NMDA receptor complex with an pharmacological advantageous profile, good central nervous system penetration property, and high solubility.

The compounds of the present invention may be useful in treatment or prevention of neurodegenerative disorders. Particularly, the compounds included in the present invention are especially useful for minimizing damage of the central nervous system arising as a consequence of ischemic or hypoxic condition such as stroke, hypoglycemia, cerebral ischemia, cardiac arrest, and physical trauma.

The compounds of the present invention are also useful in prevention of chronic neurodegenerative disorders including epilepsy, Alzheimer's disease, Huntington's disease and Parkinsonism. By virtue of their NMDA receptor antagonist properties, the present compounds may also use as anticonvulsant, analgesic, antidepressant, anxiolytic, and antischizophrenic agent.

What is claimed is:

1. A pharmaceutical composition comprising a compound of quinolinic sulfide derivatives of formula I, tautomeric forms thereof, a pharmaceutically acceptable salt thereof or a prodrug thereof:

Formula I

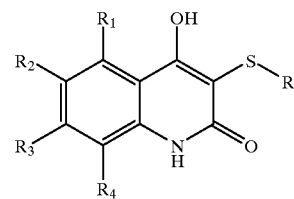

wherein R is a group of aryl of formula II, heterocycles of formula III and formula IV, or substituted-phenyl of formula V;

Formula II

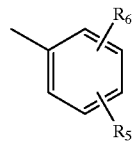

Formula III

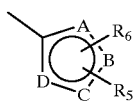

Formula IV

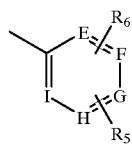

Formula V

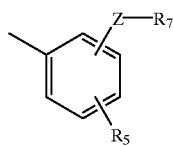

in which closed circle represents two non-adjacent double bonds in any position in five-membered ring of formula III and formula IV;

A, B, C and D independently represent oxygen, sulfur, nitrogen or carbon, provided that at least one of A, B, C, and D represents oxygen or sulfur and at least one of A, B, C, and D is other than carbon;

E, F, G, H and I independently represent oxygen, sulfur, nitrogen or carbon, provided that at least one of E, F, G, H and I represents oxygen or sulfur and at least one of E, F, G, H and I is other than carbon; and Z represents heteroatom such as nitrogen, oxygen or sulfur atom;

$R_1$, $R_2$, $R_3$, and $R_4$ independently represent hydrogen, hydroxy, halogen, nitro, amino, haloalkyl, cyano, alkyl, alkenyl, alkynyl, azido, acylamino, aryl, alkoxy, or heterocyclic ring;

$R_5$, $R_6$, and $R_7$ independently represents hydrogen, halogen, nitro, amino, carboxylate, thiol, haloalkyl, cyano, alkyl, alkenyl, alkynyl, saturated or unsaturated carbocyclic hydrocarbon, azido, acylamino, sulfonyl, aminosulfonyl, substituted or non-substituted aryl, alkoxy, substituted or non-substituted heterocyclic ring, cyclic amine, acyloxy, alkylthio, arylthio, alkylester, alkylcarboxylate, arylester, arylcarboxylate, aralkyl ester, arakylcarboxylate, urea, amidine, aralkyl, heteroarylalkyl, aryl carbonyl, aralkyl carbonyl, alkoxy carbonyl, aralkyloxy carbonyl, aryloxy carbonyl, substituted (halo)-aralkylester, substituted (halo)-arylester, substituted (halo)-arylsulfonyl, heteroarylcarbonyl, aralkylthiourea, substituted (halo)-arylthiourea, alkoxycarbonyl, iminoalkyl or iminoaralkyl, as an effective ingredient and pharmaceutically acceptable carrier with the proviso that R1, R2, R3 and R4 can not be a hydrogen simutaneously.

2. A composition of claim 1, wherein aryl groups are $C_6$–$C_{14}$ aryl groups; amino groups are $NH_2$, $NHR_8$ or $NR_8R_9$, wherein $R_8$ and $R_9$ are $C_1$–$C_6$ alkyl groups; halogen atom is fluorine, chlorine, bromine or iodine; alkyl groups are $C_1$–$C_{14}$ alkyl groups; alkenyl groups are $C_2$–$C_{14}$ alkenyl groups; alkynyl groups are $C_2$–$C_{14}$ alkynyl groups; haloalkyl groups are $C_1$–$C_6$ alkyl groups substituted by one or more fluorine, chlorine, biomine or iodine atoms; alkoxy groups are $C_1$–$C_{14}$ alkoxy groups; heterocyclic groups contain $C_3$–$C_{18}$ heterocycloalkyl, $C_3$–$C_{18}$ heterocycloalkyl ($C_1$–$C_6$)alkyl, heteroaryl and heteroaryl($C_1$–$C_6$)alkyl group.

3. A composition of claim 2, wherein aryl groups contain phenyl, naphthyl, phenanthryl, anthracyl, indenyl, azulenyl, biphenyl, biphenylenyl and fluorenyl groups;

amino groups are $NH_2$, $NHR_8$ and $NR_8R_9$, wherein $R_8$ and $R_9$ are $C_1$–$C_6$ alkyl groups, preferably $C_1$–$C_4$ alkyl groups;

halogen atoms are fluorine, chlorine, bromine and iodine;

alkyl groups are $C_1$–$C_{14}$ alkyl groups, preferably $C_1$–$C_4$ alkyl groups and contain methyl, ethyl, propyl, isopropyl, butyl, sec-butyl, and tert-butyl groups;

alkenyl groups are $C_2$–$C_{14}$ alkenyl groups, preferably $C_2$–$C_4$ alkenyl groups and contain vinyl, allyl, 1-butenyl, 2-butenyl, 3-butenyl, and isobutenyl groups;

alkynyl groups are $C_2$–$C_{14}$ alkynyl groups, preferably $C_2$–$C_4$ alkynyl groups and contain propargyl, 1-propynyl, 2-propynyl, 1-butynyl, 2-butynyl and 3-butynyl groups;

haloalkyl groups contain $C_1$–$C_6$ alkyl groups, preferably $C_1$–$C_4$ alkyl groups substituted by one or more fluorine, chlorine, bromine or iodine atoms, and contain fluoromethyl, difluoromethyl, trifluoromethyl groups;

alkoxy groups contain oxygen substituted by one of $C_1$–$C_{14}$ alkyl groups, preferably $C_1$–$C_4$ alkyl groups;

heterocyclic groups contain $C_3$–$C_{18}$ heterocycloalkyl, $C_3$–$C_8$ heterocycloalkyl ($C_1$–$C_6$) alkyl, heteroaryl and heteroaryl($C_1$–$C_6$)alkyl: suitable heterocycloalkyl groups contain piperidyl, piperazinyl and morpholinyl groups: suitable heteroaryl groups contain pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl, thiazolyl and thiadiazolyl groups.

4. A compound of quinolinic sulfide derivatives of formula I, tautomeric forms thereof, a pharmaceutically acceptable salt thereof or a prodrug thereof:

Formula I

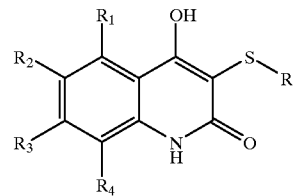

wherein R is a group of aryl of formula II, heterocycles of formula III and formula IV, or substituted-phenyl of formula V;

Formula II

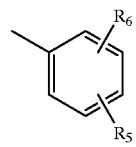

Formula III

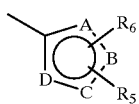

Formula IV

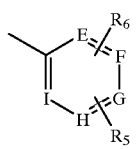

Formula V

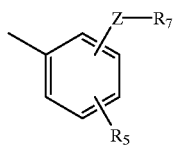

in which closed circle represents two non-adjacent double bonds in any position in five-membered ring of formula III and formula IV;

A, B, C and D independently represent oxygen, sulfur, nitrogen or carbon, provided that at least one of A, B, C, and D represents oxygen or sulfur and at least one of A, B, C, and D is other than carbon;

E, F, G, H and I independently represent oxygen, sulfur, nitrogen or carbon, provided that at least one of E, F, G, H and I represents oxygen or sulfur and at least one of E, F, G, H and I is other than carbon; and Z represents heteroatom such as nitrogen, oxygen or sulfur atom;

$R_1$, $R_2$, $R_3$, and $R_4$ independently represent hydrogen, hydroxy, halogen, nitro, amino, haloalkyl, cyano, alkyl, alkenyl, alkynyl, azido, acylamino, aryl, alkoxy, or heterocyclic ring;

$R_5$, $R_6$, and $R_7$ independently represent hydrogen, halogen, nitro, amino, carboxylate, thiol, haloalkyl, cyano, alkyl, alkenyl, alkynyl, saturated or unsaturated carbocyclic hydrocarbon, azido, acylamino, sulfonyl, aminosulfonyl, substituted or non-substituted aryl, alkoxy, substituted or non-substituted heterocyclic ring, cyclic amine, acyloxy, alkylthio, arylthio, alkylester, alkylcarboxvlate, arylester, arylcarboxylate, aralkyl ester, arakylcarboxylate, urea, amidine, aralkyl, heteroarylalkyl, aryl carbonyl, aralkyl carbonyl, alkoxy carbonyl, aralkyloxy carbonyl, aryloxy carbonyl, substituted (halo)-aralkylester, substituted (halo)-arylester, substituted (halo)-arylsulfonyl, heteroarylcarbonyl, aralkylthiourea, substituted (halo)-arylthiourea, alkoxycarbonyl, iminoalkyl or iminoaralkyl, wherein $R_1$ is hydrogen, nitro, amino, halogen or alkyl; $R_2$ is hydrogen, halogen or haloalkyl; $R_3$ is nitro, halogen or haloalkyl or alkyl; and $R_4$ is hydrogen nitro, halogen or amino.

5. A compound of claim 4, wherein $R_1$ and $R_3$ are halogens.

6. A compound of claim 5, wherein $R_1$ and $R_3$ are chlorines.

7. A compound of claim 4, wherein $R_1$ and $R_3$ are chlorine; $R_2$ and $R_4$ are hydrogens.

8. A composition of claim 1, wherein $R_5$ is hydrogen, halogen, nitro, alkyl, amino, hydroxy or alkoxy; $R_6$ is hydrogen, amino, ammonium, hydroxy, halogen, nitro, alkyl, aryl, carboxy, alkylamide, aralamide, aralkylamide or amiroalkyl; $R_7$ is aralkyl, cyclicamine, alkylamine, substituted or non-substituted heterocyclic ring, heteroarylalkyl, arylcarbonyl, aralkyl carbonyl, alkoxy carbonyl, substituted (halo)-aralkylester, substituted (halo)-arylester, substituted (halo) arylsulfonyl, heteroarylcarbonyl, aralkylthiourea, substituted (halo)-arylthiourea, iminoalkyl, or iminoaryl; and Z is oxygen or nitrogen atom.

9. A compound, which is selected from a group consisting of:

7-Chloro-4-hydroxy-3-phenylsulfanyl-1H-quinolin-2-one,
7-Chloro-4-hydroxy-3-(3-methoxy-phenylsulfanyl)-1H-quinolin-2-one,
3-(4-Bromo-phenylsulfanyl)-7-chloro-4-hydroxy-1H-quinolin-2-one,
7-Chloro-3-(3,4-dimethyl-phenylsulfanyl)-4-hydroxy-1H-quinolin-2-one,
7-Chloro-4-hydroxy-3-(3-methyl-phenylsulfanyl)-1H-quinolin-2-one,
7-Chloro-3-(2-chloro-phenylsulfanyl)-4-hydroxy-1H-quinolin-2-one,
7-Chloro-3-(2-carboxy-phenylsulfanyl)-4-hydroxy-1H-quinolin-2-one,
7-Chloro-4-hydroxy-3-(4-methyl-phenylsulfanyl)-1H-quinolin-2-one,
7-Chloro-4-hydroxy-3-(2-methyl-phenylsulfanyl)-1H-quinolin-2-one,
3-(3-Bromo-phenylsulfanyl)-7-chloro-4-hydroxy-1H-quinolin-2-one,
3-(2-Bromo-phenylsulfanyl)-7-chloro-4-hydroxy-1H-quinolin-2-one,
7-Chloro-4-hydroxy-3-(4-nitro-phenylsulfanyl)-1H-quinolin-2-one,
7-Chloro-3-(4-hydroxy-phenylsulfanyl)-4-hydroxy-1-quinolin-2-one,
7-Chloro-4-hydroxy-3-(4-phenylacetylamino-phenylsulfanyl)-1H-quinolin-2-one,
5,7-Dichloro-4-hydroxy-3-(4-methoxy-phenylsulfanyl)-1H-quinolin-2-one,
5,7-Dichloro-4-hydroxy-3-(2-methoxy-phenylsulfanyl)-1H-quinolin-2-one,
5,7-Dichloro-4-hydroxy-3-(3-methoxy-phenylsulfanyl)-1H-quinolin-2-one,
5,7-Dichloro-4-hydroxy-3-(2-methoxycarbonyl-phenylsulfanyl)-1H-quinolin-2-one,
3-(2-Carboxy-phenylsulfanyl)-5,7-dichloro-4-hydroxy-1H-quinolin-2-one,
3-(2-Bromo-phenylsulfanyl)-5,7-dichloro-4-hydroxy-1H-quinolin-2-one,
5,7-Dichloro-4-hydroxy-3-(2-methyl-phenylsulfanyl)-1H-quinolin 2-one,
3-(2-Chloro-phenylsulfanyl)-5,7-dichloro-4-hydroxy--1H-quinolin-2-one,
5,7-Dichloro-4-hydroxy-3-(4-hydroxy-phenylsulfanyl)-1H-quinolin-2-one,
3-(4-Amino-phenylsulfanyl)-5,7-dichloro-4-hydroxy-1H-quinolin-2-one hydrochloride,
3-(Benzothiazole-2-ylsulfanyl)-7-chloro-4-hydroxy-1-H-quinolin-2-one,
3-(Benzoxazole-2-ylsulfanyl)-7-chloro-4-hydroxy-1H-quinolin-2 one,
7-Chloro-4-hydroxy-3-(1-methyl-1H-imidazole-2-ylsulfanyl)-1H-quinolin-2-one, 3-(1H-Benzoimidazole-2-ylsulfanyl)-7-chloro-4-hydroxy-1H-quinolin-2-one, 7-Chloro-4-hydroxy-3-(1H-[1.2.4]triazol-3-ylsulfanyl)-1H-quinolin-2-one, 5,7-Dichloro-4-hydroxy-3-(nicotine-2-ylsulfanyl)-1H-quinolin-2-one, 5,7-Dichloro-4-hydroxy-3-(nicotine-6-ylsulfanyl)-1H-quinolin-2-one, 5,7-Dichloro-4-hydroxy-3-(5-N-benzylcarbamoyl-pyridine-2-ylsufanyl)-1H-quinolin-2-one, 7-Chloro-4-hydroxy-3-(nicotine-2-ylsufanyl)-1H-quinolin-2-one, 5,7-Dichloro-4-hydroxy-3-[1-(4-hydroxy-phenyl)-1H-tetrazole-5-ylsulfanyl]-1H-quinolin-2-one, 5,7-Dichloro-4-hydroxy-3-(1H-[1.2.4]triazole-3-ylsulfanyl)-1H-quinolin-2-one, 3-(4-Benzyloxy-phenylsulfanyl)-5,7-dichloro 4-hydroxy-1H-quinolin-2-one, 5,7-Dichloro-4-hydroxy-3-[4-(piperidin-4-yloxy)-phenyl sulfanyl]-1H-quinolin-2-one hydrochloride, 5,7-Dichloro-4-hydroxy-3-[4-(2-piperidin-1-ylethoxy)-phenylsufanyl]-1-H-quinolin-2-one, 5,7-Dichloro-4-hydroxy-3-[4-(2-pyridin-2-ylethoxy)-phenylsulfanyl]-1H-quinolin-2-one, 7-Chloro-4-hydroxy-3-(4-phenylacetylamino-phenylsulfanyl)-1H-quinolin-2-one, 5,7-Dichloro-4-hydroxy-3-(4-phenylacetylamido-phenylsulfanyl)-1H-quinolin-2-one, 3-[4-{2-(3-Bromophenyl)acetamido}-phenylsulfanyl]-5,7-dichloro-4-hydroxy-1H-quinolin-2-one, 3-[4-(3-Chlorophenylamido)-phenylsulfanyl]-5,7-dichloio-4-hydroxy-1H-quinolin-2-one, 3-[4-(4-Chlorophenylsulfonamido)-phenylsulfanyl]-5,7-dichloro-4-hydroxy-1H-quinolin-2-one, 5,7-Dichloro-4-hydroxy-3-[4-(nicotinamido)-phenylsulfanyl]-1H-quinolin-2-one, 5,7-Dichloro-3-[4-(2-furamido)-phenylsulfanyl)-4-hydroxy-1H-quinolin-2-one, 3-(4-Benzylthioureido-phenylsulfanyl)-5,7-dichloro-4-hydroxy-1H-quinolin-2-one, 3-[4-{(3-chlorophenyl)-thioureido}-phenylsulfanyl]-5,7-dichloro-4-hydroxy-1H-quinolin-2-one, 5,7-Dichloro-4-hydroxy-3-[4-(isobutoxy-carbonyl)amino-phenylsulfanyl]-1H-quinolin-2-one, 5,7-Dichloro-3-[4-(4-chloro-benzylamino)-phenylsulfanyl]-4-hydroxy-1H quinolin-2-one hydrochloride, 3-(4-Amino-phenylsulfanyl)-5,7-dichloro-4-hydroxy-1H-quinolin-2-one hydrochloride, 5,7-Dichloro-4-hydroxy-3-[4-(1-imino-ethylamino)-phenylsulfanyl]-1H-quinolin-2-one hydrochloride, 5,7-Dichloro-4-hydroxy-3-{4-[(imino-phenyl-methyl)-amino]-phenylsulfanyl}-1H-quinolin-2-one and pharmaceutically salts and prodrugs thereof.

10. A compound of quinolinic sulfide derivatives of formula I, tautomeric forms thereof, a pharmaceutically acceptable salt thereof or a prodrug thereof:

Formula I

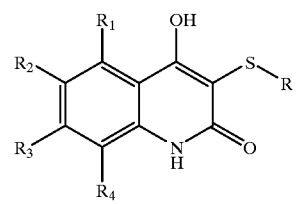

wherein R is a group of aryl of formula II, heterocycles of formula III and formula IV, or substituted-phenyl of formula V;

Formula II

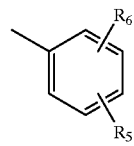

Formula III

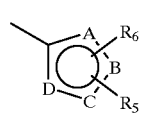

Formula IV

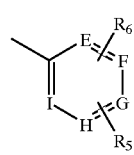

Formula V

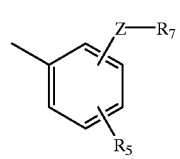

in which closed circle represents two non-adjacent double bonds in any position in five-membered ring of formula III and formula IV;

A, B, C and D independently represent oxygen, sulfur, nitrogen or carbon, provided that at least one of A, B, C and D represents oxygen or sulfur and at least one of A, B, C and D is other than carbon;

E, F, G, H and I independently represent oxygen, sulfur, nitrogen or carbon, provided that at least one of E, F, G, H and I represents oxygen or sulfur and at least one of E, F, G, H and I is other than carbon; and Z represents heteroatom such as nitrogen, oxygen or sulfur atom;

$R_1$, $R_2$, and $R_4$ independently represent hydrogen, hydroxy, halogen, nitro, amino, haloalkyl, cyano, alkyl, alkenyl, alkynyl, azido, acylamino, aryl, alkoxy, or heterocyclic ring; and $R_3$ is Cl;

$R_5$, $R_6$ and $R_7$ independently represents hydrogen, halogen, nitro, amino, carboxylate, thiol, haloalkyl, cyano, alkyl, alkenyl, alkynyl, saturated or unsaturated carbocyclic hydrocarbon, azido, acylamino, sulfanyl, aminosulfonyl, substituted or non-substituted aryl, alkoxy, substituted or non-substituted heterocyclic ring, cyclic amine, acyloxy, alkylthio, arylthio, alkylester, alkylcarboxylate, arylester, arylcarboxylate, aralkylester, aralkylcarboxylate, urea, amidine, aralkyl, heteroarylalkyl, aryl carbonyl, aralkyl carbonyl, alkoxy carbonyl, aralkyloxy carbonyl, aryloxy carbonyl, substituted (halo)-aralkylester, substituted (halo)-arylester, substituted (halo)-arylsulfonyl, heteroarylcarbonyl, aralkylthiourea, substituted (halo)-aryltihiourea, alkoxycarbonyl, iminoalkyl or iminoaralkyl.

11. The composition as defined in claim 1, effective as an antagonist of excitatory amino acid for NMDA receptor.

12. The method for treatment of ischemic, hypoxic or hypo-glycemic central nervous system damage which comprises administering a composition as defined in claim 1.

13. The method for treatment of epilepsy, stroke, Alzheimer's disease, Huntington's disease and Parkinsonism comprising administering a composition as defined in claim 1.

14. The composition as defined in claim 1, effective as anticonvulsant, analgesic, antidepressant, antianxiolytic, and antischizophrenic agent.

15. A process for preparation of a compound
of quinolinic sulfide derivatives of formula I, tautomeric forms thereof, a pharmaceutically acceptable salt thereof or a prodrug thereof:

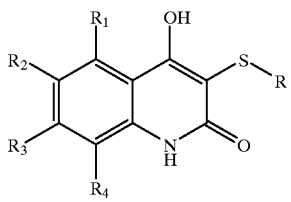

wherein R is a group of aryl of formula II, heterocycles of formula III and formula IV, or substituted-phenyl of formula V;

Formula II

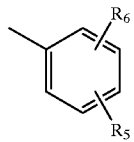

Formula III

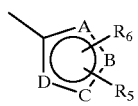

Formula IV

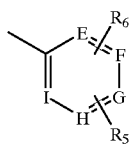

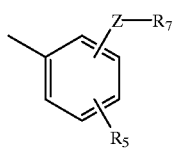

in which closed circle represents two non-adjacent double bonds in any position in five-membered ring of formula III and formula IV;

A, B, C and D independently represent oxygen, sulfur, nitrogen or carbon, provided that at least one of A, B, C, and D represents oxygen or sulfur and at least one of A, B, C, and D is other than carbon;

E, F, G, H and I independently represent oxygen, sulfur, nitrogen or carbon, provided that at least one of E, F, G, H and I represents oxygen or sulfur and at least one of E, F, G, H and I is other than carbon; and Z represents heteroatom such as nitrogen, oxygen or sulfur atom;

$R_1$, $R_2$, $R_3$, and $R_4$ independently represent hydrogen, hydroxy, halogen, nitro, amino, haloalkyl, cyano, alkyl, alkenyl, alkynyl azido, acylamino, aryl, alkoxy, or heterocyclic ring;

$R_1$, $R_2$, $R_3$, and $R_4$ independently represents hydrogen, hydroxy, halogen, nitro, amino, haloalkyl, cyano, alkyl, alkenyl, alkynyl, azido, acylamino, aryl, alkoxy, or heterocyclic ring;

$R_5$, $R_6$, and $R_7$ independently represents hydrogen, halogen, nitro, amino, carboxylate, thiol, haloalkyl, cyano, alkyl, alkenyl, alkynyl, saturated or unsaturated carbocyclic hydrocarbon, azido, acylamino, sulfonyl, aminosulfonyl, substituted or non-substituted aryl, alkoxy, substituted or non-substituted heterocyclic ring, cyclic amine, acyloxy, alkylthio, arylthio, alkylester, alkylcarboxylate, arylester, arylcarboxylate, aralkyl ester, aralkylcarboxylate, urea, amidine, aralkyl, heteroarylalkyl, aryl carbonyl, aralkyl carbonyl, alkoxy carbonyl, aralkyloxy carbonyl, aryloxy carbonyl, substituted (halo)-aralkylester, substituted (halo)-arylester, substituted (halo)-arylsulfonyl, heteroarylcarbonyl, aralkylthiourea, substituted (halo)-arylthiourea, alkoxycarbonyl, iminoalkyl or iminoaralkyl, which process comprises:

1) preparing a compound of formula VII by reacting a compound of formula XII with chloroacetyl chloride or bromoacetyl chloride (step I);

2) preparing a compound of formula VI by reacting a compound of formula VII with a compound of formula VIII; or by reacting a compound of formula X with a compound of formula XI, wherein the formula X is prepared by reacting a compound of formula VI with a compound of formula IX (step II); and 3) preparing a compound of formula I by cyclization of a compound of formula VI (step III);

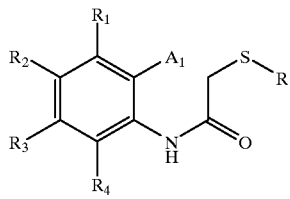

$A_1$ include esters, acid anhydrides, acid halides, orthoesters, or primary, secondary or tertiary amides,

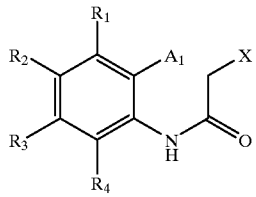

Formula VIII

HS—R

Formula IX

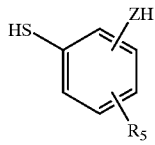

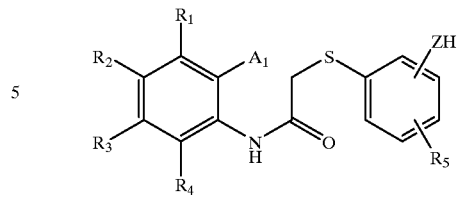

Formula XI

Y—$R_7$

X represents halogen atom and Y represents a consumed unit such as chlorine, oxygen atom or hydroxy group in process of forming a Z—$R_7$ bond,

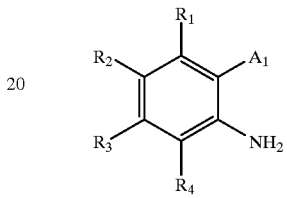

16. A process of claim 15, wherein a compound of formula I is prepared by reacting a compound of formula XI with a compound of formula XIII, which is obtained by cyclization of a compound of formula X.

Formula XIII

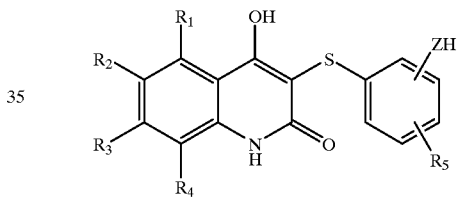

* * * * *